(12) United States Patent
Nakamura

(10) Patent No.: US 11,027,044 B2
(45) Date of Patent: Jun. 8, 2021

(54) METHOD FOR PRODUCING SHEET-LIKE CELL STRUCTURE AND SHEET-LIKE CELL STRUCTURE

(71) Applicant: FUJIFILM Corporation, Tokyo (JP)

(72) Inventor: Kentaro Nakamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 285 days.

(21) Appl. No.: 15/941,187

(22) Filed: Mar. 30, 2018

(65) Prior Publication Data

US 2018/0280576 A1    Oct. 4, 2018

Related U.S. Application Data

(63) Continuation of application No. PCT/JP2016/078779, filed on Sep. 29, 2016.

(30) Foreign Application Priority Data

Sep. 30, 2015    (JP) .............................. JP2015-192785

(51) Int. Cl.
*A61L 27/38*    (2006.01)
*A61L 27/50*    (2006.01)
(Continued)

(52) U.S. Cl.
CPC .............. *A61L 27/38* (2013.01); *A61L 27/222* (2013.01); *A61L 27/50* (2013.01); *A61L 27/52* (2013.01);
(Continued)

(58) Field of Classification Search
CPC ........ A61L 27/38; A61L 27/50; A61L 27/222; A61L 27/52; C07K 14/78; C12N 2533/54;
(Continued)

(56) References Cited

U.S. PATENT DOCUMENTS

2012/0100612 A1    4/2012  Takahashi et al.
2012/0329157 A1*   12/2012 Nakamura .............. A61L 27/38
                                                   435/397
2013/0203159 A1    8/2013  Itoh et al.

FOREIGN PATENT DOCUMENTS

CN    102858381 A    1/2013
CN    103119151 A    5/2013
(Continued)

OTHER PUBLICATIONS

Isenberg et al., A thermoresponsive, microtextured substrate for cell sheet engineering with defined structural organization. Biomaterials, Vo. 29, No. 17 (Jun. 2008) pp. 2565-2572. (Year: 2008).*
(Continued)

*Primary Examiner* — Kara D Johnson
(74) *Attorney, Agent, or Firm* — Sughrue Mion, PLLC

(57) ABSTRACT

An object of the present invention is to provide a method for producing a sheet-like cell structure having excellent strength and shape-maintaining performance, and a sheet-like cell structure having excellent strength and shape-maintaining performance. According to the present invention, there is provided a method for producing a sheet-like cell structure, including: a step of adding a biocompatible macromolecular block, a cell, and a liquid medium onto a culture support body having a plurality of recessed portions on a culture surface, and immersing the biocompatible macromolecular block and the cell in uppermost portions of the recessed portions; and a step of culturing the cell to obtain a sheet-like cell structure.

11 Claims, 9 Drawing Sheets

Specification includes a Sequence Listing.

(51) Int. Cl.
  *A61L 27/22* (2006.01)
  *A61L 27/52* (2006.01)
  *C07K 14/78* (2006.01)

(52) U.S. Cl.
  CPC .......... *C07K 14/78* (2013.01); *C12N 2533/00* (2013.01); *C12N 2533/30* (2013.01); *C12N 2533/40* (2013.01); *C12N 2533/54* (2013.01); *C12N 2533/72* (2013.01); *C12N 2533/78* (2013.01); *C12N 2533/80* (2013.01)

(58) Field of Classification Search
  CPC ............ C12N 2533/30; C12N 2533/40; C12N 2533/72; C12N 2533/78; C12N 2533/80
  See application file for complete search history.

(56) References Cited

FOREIGN PATENT DOCUMENTS

| | | |
|---|---|---|
| JP | 2011-004612 A | 1/2011 |
| JP | 2011-006490 A | 1/2011 |
| JP | 2011-234646 A | 11/2011 |
| JP | 2015-073520 A | 4/2015 |
| WO | 2011/108517 A1 | 9/2011 |
| WO | 2012/036011 A1 | 3/2012 |

OTHER PUBLICATIONS

Nikkhah et al., Engineering microscale topographies to control the cell-substrate interface. Biomaterials, vol. 33, No. 21 (Jul. 2012) pp. 5230-5246. (Year: 2012).*

Hideo Yokoyama et al., "Formation of Three-dimensional tissue using spheroid fusion", Abstracts of Autumn Meeting of the Society of Chemical Engineers, Japan (CD-ROM), Sep. 9, 2015, vol. 47, ZB1P64, total 4 pages.

Satoshi Shiramizu et al., "Assembly of cell sheet tissue by spheroid fusion", Abstracts of Autumn Meeting of the Society of Chemical Engineers, Japan (CD-ROM), 2014, vol. 46, ZA1P31, total 4 pages.

International Search Report of PCT/JP2016/078779 dated Dec. 27, 2016.

Written Opinion of the International Searching Authority dated Dec. 27, 2016, in counterpart International Application No. PCT/JP2016/078779.

International Preliminary Report on Patentability dated Apr. 3, 2018, in counterpart International Application No. PCT/JP2016/078779.

Office Action dated Oct. 30, 2020, from the State Intellectual Property Office of the P.R.C in Chinese application No. 201680058112.X.

* cited by examiner

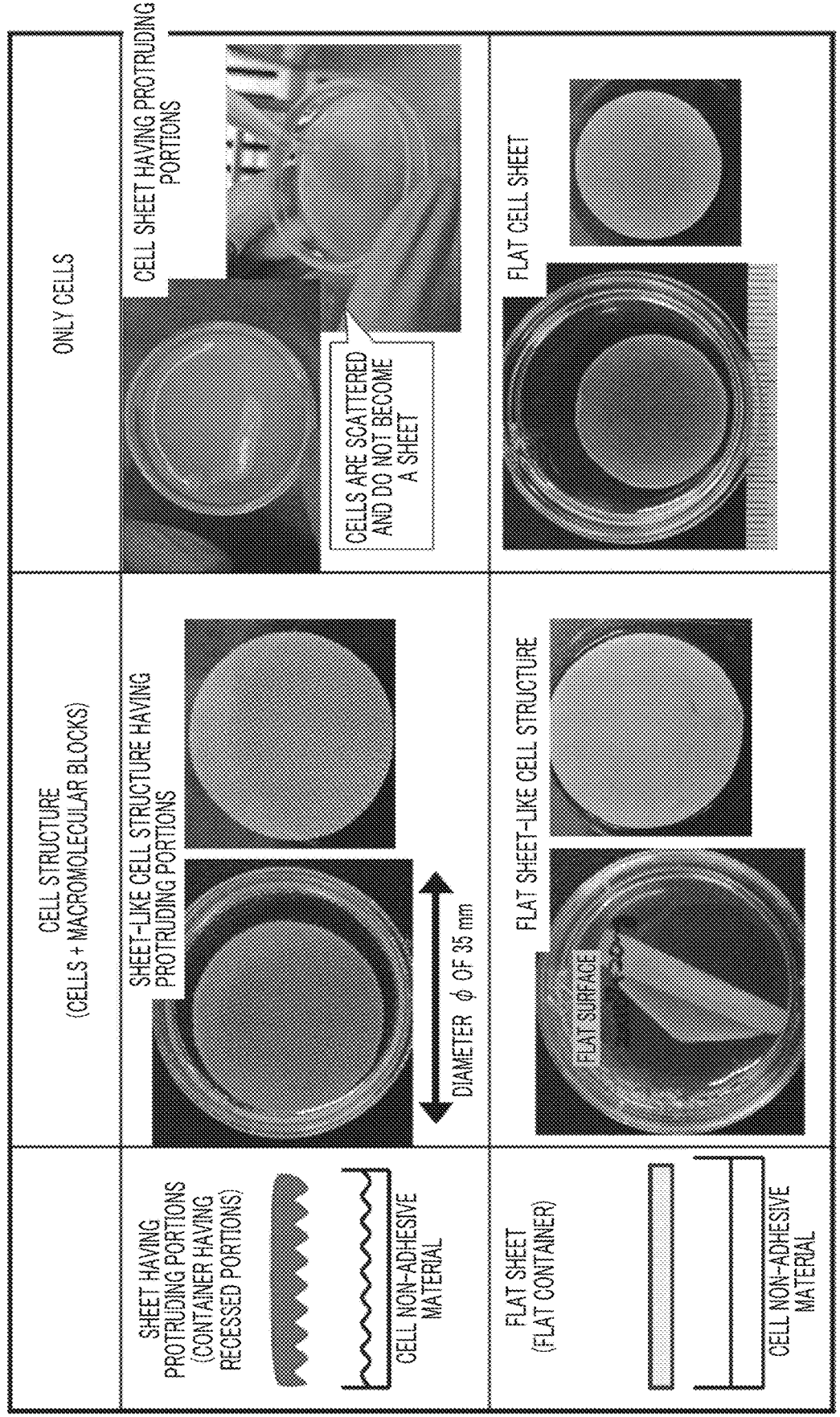

SEQUENCE LISTING

<160> NUMBER OF SEQ ID NOS: 11

<210> SEQ ID NO 1
<211> LENGTH: 571
<212> TYPE: PRT
<213> ORGANISM: Artificial Sequence
<220> FEATURE:
<223> OTHER INFORMATION: recombinant gelatin

<400> SEQUENCE: 1

```
Gly Ala Pro Gly Ala Pro Gly Leu Gln Gly Ala Pro Gly Leu Gln Gly
 1               5                  10                  15

Met Pro Gly Glu Arg Gly Ala Ala Gly Leu Pro Gly Pro Lys Gly Glu
                20                  25                  30

Arg Gly Asp Ala Gly Pro Lys Gly Ala Asp Gly Ala Pro Gly Ala Pro
            35                  40                  45

Gly Leu Gln Gly Met Pro Gly Glu Arg Gly Ala Ala Gly Leu Pro Gly
        50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
               100                 105                 110

Asp Ala Gly Pro Lys Gly Ala Asp Gly Ala Pro Gly Lys Asp Gly Val
           115                 120                 125

Arg Gly Leu Ala Gly Pro Ile Gly Pro Pro Gly Pro Ala Gly Ala Pro
       130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
            260                 265                 270

Asp Gly Val Arg Gly Leu Ala Gly Pro Ile Gly Pro Pro Gly Glu Arg
        275                 280                 285

Gly Ala Ala Gly Leu Pro Gly Pro Lys Gly Glu Arg Gly Asp Ala Gly
    290                 295                 300
```

```
Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
            340                 345                 350

Pro Lys Gly Glu Arg Gly Asp Ala Gly Pro Lys Gly Ala Asp Gly Ala
        355                 360                 365

Pro Gly Lys Asp Gly Val Arg Gly Leu Ala Gly Pro Pro Gly Ala Pro
    370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Ala Gly Pro
                405                 410                 415

Lys Gly Ala Asp Gly Ala Pro Gly Ala Pro Gly Leu Gln Gly Met Pro
            420                 425                 430

Gly Glu Arg Gly Ala Ala Gly Leu Pro Gly Pro Lys Gly Glu Arg Gly
        435                 440                 445

Asp Ala Gly Pro Lys Gly Ala Asp Gly Ala Pro Gly Lys Asp Gly Val
    450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Ala Gly Pro Lys Gly
                485                 490                 495

Ala Asp Gly Ala Pro Gly Lys Asp Gly Val Arg Gly Leu Ala Gly Pro
            500                 505                 510

Ile Gly Pro Pro Gly Pro Ala Gly Ala Pro Gly Ala Pro Gly Leu Gln
        515                 520                 525

Gly Met Pro Gly Glu Arg Gly Ala Ala Gly Leu Pro Gly Pro Lys Gly
    530                 535                 540

Glu Arg Gly Asp Ala Gly Pro Lys Gly Ala Asp Gly Ala Pro Gly Lys
545                 550                 555                 560

Asp Gly Val Arg Gly Leu Ala Gly Pro Pro Gly
                565                 570

<210> SEQ ID NO 2
<211> LENGTH: 4
<212> TYPE: PRT
<213> ORGANISM: Artificial Sequence
<220> FEATURE:
<223> OTHER INFORMATION: adhesive sequence

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: adhesive sequence

<400> SEQUENCE: 3

Tyr Ile Gly Ser Arg
1               5
```

```
<210> SEQ ID NO 4
<211> LENGTH: 5
<212> TYPE: PRT
<213> ORGANISM: Artificial Sequence
<220> FEATURE:
<223> OTHER INFORMATION: adhesive sequence

<400> SEQUENCE: 4

Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: adhesive sequence

<400> SEQUENCE: 5

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: adhesive sequence

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: adhesive sequence

<400> SEQUENCE: 7

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: adhesive sequence

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 9

Asp Gly Glu Ala
1
```

```
<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 10

Glu Arg Gly Asp
1

<210> SEQ ID NO 11
<211> LENGTH: 571
<212> TYPE: PRT
<213> ORGANISM: Artificial Sequence
<220> FEATURE:
<223> OTHER INFORMATION: CBE
<220> FEATURE:
<221> NAME/KEY: MISC_FEATURE
<222> LOCATION: (1)..(571)
<223> OTHER INFORMATION: all Xaa is independently any amino acid

<400> SEQUENCE: 11

Gly Ala Pro Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
            20                  25                  30

Xaa Gly Xaa Xaa Gly Xaa Xaa Gly Xaa Xaa Gly Xaa Xaa Gly Xaa Xaa
        35                  40                  45

Gly Xaa Xaa Gly Xaa Xaa Gly Xaa Xaa Gly Xaa Xaa Gly Xaa Xaa Gly
    50                  55                  60

Xaa Xaa Gly Xaa Xaa Gly Xaa Xaa Gly Xaa Xaa Gly Xaa Xaa Gly Xaa
65                  70                  75                  80

Xaa Gly Xaa Xaa Gly Xaa Xaa Gly Xaa Xaa Gly Xaa Xaa Gly Xaa Xaa
            85                  90                  95

Gly Xaa Xaa Gly Xaa Xaa Gly Xaa Xaa Gly Xaa Xaa Gly Xaa Xaa Gly
            100                 105                 110

Xaa Xaa Gly Xaa Xaa Gly Xaa Xaa Gly Xaa Xaa Gly Xaa Xaa Gly Xaa
        115                 120                 125

Xaa Gly Xaa Xaa Gly Xaa Xaa Gly Xaa Xaa Gly Xaa Xaa Gly Xaa Xaa
    130                 135                 140

Gly Xaa Xaa Gly Xaa Xaa Gly Xaa Xaa Gly Xaa Xaa Gly Xaa Xaa Gly
145                 150                 155                 160

Xaa Xaa Gly Xaa Xaa Gly Xaa Xaa Gly Xaa Xaa Gly Xaa Xaa Gly Xaa
                165                 170                 175

Xaa Gly Xaa Xaa Gly Xaa Xaa Gly Xaa Xaa Gly Xaa Xaa Gly Xaa Xaa
            180                 185                 190

Gly Xaa Xaa Gly Xaa Xaa Gly Xaa Xaa Gly Xaa Xaa Gly Xaa Xaa Gly
        195                 200                 205

Xaa Xaa Gly Xaa Xaa Gly Xaa Xaa Gly Xaa Xaa Gly Xaa Xaa Gly Xaa
    210                 215                 220

Xaa Gly Xaa Xaa Gly Xaa Xaa Gly Xaa Xaa Gly Xaa Xaa Gly Xaa Xaa
225                 230                 235                 240

Gly Xaa Xaa Gly Xaa Xaa Gly Xaa Xaa Gly Xaa Xaa Gly Xaa Xaa Gly
                245                 250                 255

Xaa Xaa Gly Xaa Xaa Gly Xaa Xaa Gly Xaa Xaa Gly Xaa Xaa Gly Xaa
            260                 265                 270

Xaa Gly Xaa Xaa Gly Xaa Xaa Gly Xaa Xaa Gly Xaa Xaa Gly Xaa Xaa
```

-continued

```
              275                 280                 285
Gly Xaa Xaa Gly Xaa Xaa Gly Xaa Xaa Gly Xaa Xaa Gly Xaa Xaa Gly
    290                 295                 300
Xaa Xaa Gly Xaa Xaa Gly Xaa Xaa Gly Xaa Xaa Gly Xaa Xaa Gly Xaa
305                 310                 315                 320
Xaa Gly Xaa Xaa Gly Xaa Xaa Gly Xaa Xaa Gly Xaa Xaa Gly Xaa Xaa
                325                 330                 335
Gly Xaa Xaa Gly Xaa Xaa Gly Xaa Xaa Gly Xaa Xaa Gly Xaa Xaa Gly
            340                 345                 350
Xaa Xaa Gly Xaa Xaa Gly Xaa Xaa Gly Xaa Xaa Gly Xaa Xaa Gly Xaa
        355                 360                 365
Xaa Gly Xaa Xaa Gly Xaa Xaa Gly Xaa Xaa Gly Xaa Xaa Gly Xaa Xaa
    370                 375                 380
Gly Xaa Xaa Gly Xaa Xaa Gly Xaa Xaa Gly Xaa Xaa Gly Xaa Xaa Gly
385                 390                 395                 400
Xaa Xaa Gly Xaa Xaa Gly Xaa Xaa Gly Xaa Xaa Gly Xaa Xaa Gly Xaa
                405                 410                 415
Xaa Gly Xaa Xaa Gly Xaa Xaa Gly Xaa Xaa Gly Xaa Xaa Gly Xaa Xaa
            420                 425                 430
Gly Xaa Xaa Gly Xaa Xaa Gly Xaa Xaa Gly Xaa Xaa Gly Xaa Xaa Gly
        435                 440                 445
Xaa Xaa Gly Xaa Xaa Gly Xaa Xaa Gly Xaa Xaa Gly Xaa Xaa Gly Xaa
    450                 455                 460
Xaa Gly Xaa Xaa Gly Xaa Xaa Gly Xaa Xaa Gly Xaa Xaa Gly Xaa Xaa
465                 470                 475                 480
Gly Xaa Xaa Gly Xaa Xaa Gly Xaa Xaa Gly Xaa Xaa Gly Xaa Xaa Gly
                485                 490                 495
Xaa Xaa Gly Xaa Xaa Gly Xaa Xaa Gly Xaa Xaa Gly Xaa Xaa Gly Xaa
            500                 505                 510
Xaa Gly Xaa Xaa Gly Xaa Xaa Gly Xaa Xaa Gly Xaa Xaa Gly Xaa Xaa
        515                 520                 525
Gly Xaa Xaa Gly Xaa Xaa Gly Xaa Xaa Gly Xaa Xaa Gly Xaa Xaa Gly
    530                 535                 540
Xaa Xaa Gly Xaa Xaa Gly Xaa Xaa Gly Xaa Xaa Gly Xaa Xaa Gly Xaa
545                 550                 555                 560
Xaa Gly Xaa Xaa Gly Xaa Xaa Gly Xaa Xaa Gly
                565                 570
```

METHOD FOR PRODUCING SHEET-LIKE CELL STRUCTURE AND SHEET-LIKE CELL STRUCTURE

CROSS-REFERENCE TO RELATED APPLICATIONS

This application is a Continuation of PCT International Application No. PCT/JP2016/078779 filed on Sep. 29, 2016, which claims priority under 35 U.S.C § 119(a) to Japanese Patent Application No. 2015-192785 filed on Sep. 30, 2015. Each of the above application(s) is hereby expressly incorporated by reference, in its entirety, into the present application.

BACKGROUND OF THE INVENTION

1. Field of the Invention

The present invention relates to a method for producing a sheet-like cell structure and a sheet-like cell structure.

2. Description of the Related Art

Currently, regenerative medicine, which regenerates living body tissues and organs having functional disorders or dysfunction, is put into practical use. The regenerative medicine is new medical technology creating a form or a function of a living body tissue that cannot be recovered with only natural healing ability possessed by a living body, which is the same as that of an original tissue, again, using three factors including a cell, a scaffold, and a growth factor. In recent years, treatment using cells is gradually realized. For example, in a case of performing regenerative medicine in which cells are used for treating cardiomyopathy or the like, in some cases, cell sheet engineering may be used from the viewpoint of easy attachment to the surface of an organ (for example, JP2011-6490A).

In addition, a cell structure, which contains cells and macromolecular blocks having biocompatibility, and in which the plurality of the above-described macromolecular blocks are arranged in gaps between the plurality of the above-described cells, is disclosed in WO2011/108517A. In the cell structure disclosed in WO2011/108517A, it is possible to deliver nutrients to the inside of the cell structure from the outside. The cell structure has a sufficient thickness, and cells exist in the structure uniformly. In example of WO2011/108517A, high cell survival activity is verified using a macromolecular block formed of a recombinant gelatin material or a natural gelatin material.

On the other hand, WO2012/036011A discloses a culture substrate in which a plurality of recessed portions forming compartments in which an object to be cultured is cultured are formed on the surface of the culture substrate, and the surface of the culture substrate between the recessed portions adjacent to each other is a non-flat surface, and discloses that spheroid culture is carried out using this culture substrate. JP2015-73520A discloses a cell culture container for performing spheroid culture which includes: a culture surface on which a plurality of recessed portions forming compartments in which an object to be cultured is cultured are formed; a container main body including the culture surface on a bottom surface, and a liquid-permeable lid body which is placed on the top portions of the plurality of recessed portions and closes the openings of the recessed portions, in which the top portion of the culture surface between the recessed portions adjacent to each other, the liquid-permeable lid body is disposed so that the distance from the top portion between the recessed portions in a state of being immersed in a culture liquid in the container main body is smaller than the outer diameter dimension of the object to be cultured which has been cultured in the recessed portions.

SUMMARY OF THE INVENTION

In the case of the cell sheet described in JP2011-6490A, nutrients and oxygen do not reach cells, and therefore, there is a problem that it is impossible to produce a cell sheet having a sufficient thickness. A method for producing a cell structure containing a biocompatible macromolecular block and a cell is disclosed in WO2011/108517A. However, the production of a sheet having excellent strength and shape-maintaining performance is not specifically disclosed. It is disclosed in WO2012/036011A and JP2015-73520A that spheroid culture is carried out using a predetermined cell culture container, but there is no disclosure of production of a cell sheet.

As described above, it is desired to establish a method for producing a sheet containing cells and having excellent strength and shape-maintaining performance. An object of the present invention is to provide a method for producing a sheet-like cell structure having excellent strength and shape-maintaining performance, and a sheet-like cell structure having excellent strength and shape-maintaining performance.

The present inventors have conducted extensive studies to solve the above-described problem, and as a result, they have found that it is possible to produce a sheet-like cell structure having excellent strength and shape-maintaining performance by adding biocompatible macromolecular block, cells, and a liquid medium onto a culture support body having a plurality of recessed portions on a culture surface and immersing the biocompatible macromolecular blocks and the cells in uppermost portions of the recessed portions to culture the cells in the above-described state. The present invention has been completed based on the finding.

That is, according to the present invention, the following inventions are provided.

(1) A method for producing a sheet-like cell structure, comprising: a step of adding a biocompatible macromolecular block, cell, and a liquid medium onto a culture support body having a plurality of recessed portions on a culture surface, and immersing the biocompatible macromolecular block and the cell in uppermost portions of the recessed portions; and a step of culturing the cell to obtain a sheet-like cell structure.

(2) The method for producing a sheet-like cell structure according to (1), in which the culture support body has recessed portions having a depth of 10 μm to 1,500 μm and a diameter of 10 μm to 1,500 μm.

(3) The method for producing a sheet-like cell structure according to (1) or (2), in which the area of the recessed portions on the culture surface is larger than or equal to 70% with respect to the whole area of the culture surface.

(4) The method for producing a sheet-like cell structure according to (1) or (2), in which a surface of the culture support body between the recessed portions adjacent to each other is non-flat.

(5) The method for producing a sheet-like cell structure according to any one of (1) to (4), in which a thickness of a thinnest portion of the sheet-like cell structure is 50 μm to 5 mm.

(6) The method for producing a sheet-like cell structure according to any one of (1) to (5), in which the culture surface of the culture support body is subjected to a treatment for suppressing adhesion of cells.
(7) The method for producing a sheet-like cell structure according to any one of (1) to (6), in which a size of the biocompatible macromolecular block is 1 μm to 700 μm.
(8) The method for producing a sheet-like cell structure according to any one of (1) to (7), in which biocompatible macromolecules are recombinant gelatin.
(9) The method for producing a sheet-like cell structure according to (8), in which the recombinant gelatin is represented by the following formula A-[(Gly-X-Y)n]m-B     Formula:

in the formula, A represents an arbitrary amino acid or an amino acid sequence, B represents an arbitrary amino acid or an amino acid sequence, n pieces of X each independently represent any amino acid, n pieces of Y each independently represent any amino acid, and n represents an integer of 3 to 100, m represents an integer of 2 to 10, and n pieces of Gly-X-Y may be the same as or different from each other.
(10) The method for producing a sheet-like cell structure according to (8) or (9), in which the recombinant gelatin is any one of a peptide formed of an amino acid sequence described in SEQ ID No: 1; a peptide which is formed of an amino acid sequence in which one or several amino acids are deleted, substituted, or added in the amino acid sequence described in SEQ ID No: 1, and has biocompatibility; and a peptide which is formed of an amino acid sequence having 80% or more sequence identity to the amino acid sequence described in SEQ ID No: 1, and has biocompatibility.
(11) A sheet-like cell structure comprising: a biocompatible macromolecular block; and a cell, in which the sheet-like cell structure has a plurality of protruding portions on at least a single surface thereof, and a plurality of the above-described biocompatible macromolecular blocks are arranged in gaps between a plurality of the cells in the protruding portions.
(12) The sheet-like cell structure according to (11), further comprising: protruding portions having a height of 10 μm to 2,000 μm and a diameter of 10 μm to 2,000 μm.
(13) The sheet-like cell structure according to (11) or (12), in which a thickness of a thinnest portion is 50 μm to 5 mm.
(14) The sheet-like cell structure according to any one of (11) to (13), in which biocompatible macromolecules are recombinant gelatin.
(15) The sheet-like cell structure according to (14), in which the recombinant gelatin is represented by the following formula A-[(Gly-X-Y)n]m-B     Formula:

in the formula, A represents an arbitrary amino acid or an amino acid sequence, B represents an arbitrary amino acid or an amino acid sequence, n pieces of X each independently represent any amino acid, n pieces of Y each independently represent any amino acid, and n represents an integer of 3 to 100, m represents an integer of 2 to 10, and n pieces of Gly-X-Y may be the same as or different from each other.
(16) The sheet-like cell structure according to (14) or (15), in which the recombinant gelatin is any one of a peptide formed of an amino acid sequence described in SEQ ID No: 1; a peptide which is formed of an amino acid sequence in which one or several amino acids are deleted, substituted, or added in the amino acid sequence described in SEQ ID No: 1, and has biocompatibility; and a peptide which is formed of an amino acid sequence having 80% or more sequence identity to the amino acid sequence described in SEQ ID No: 1, and has biocompatibility.

According to the method for producing a sheet-like cell structure of the present invention, it is possible to produce a sheet-like cell structure having excellent strength and shape-maintaining performance.

The sheet-like cell structure of the present invention has excellent strength and shape-maintaining performance. Therefore, the handleability improves, and it is easy to install the sheet-like cell structure on the surface of an organ.

BRIEF DESCRIPTION OF THE DRAWINGS

FIG. 2A shows an example without a cell adhesion suppressant layer and FIG. 2B shows an example with the cell adhesion suppressant layer.

FIG. 3A shows an example without a cell adhesion suppressant layer and FIG. 3B shows an example with the cell adhesion suppressant layer.

FIG. 12 shows a summary of the results of examples and comparative examples.

DESCRIPTION OF THE PREFERRED EMBODIMENTS

Figure 1:
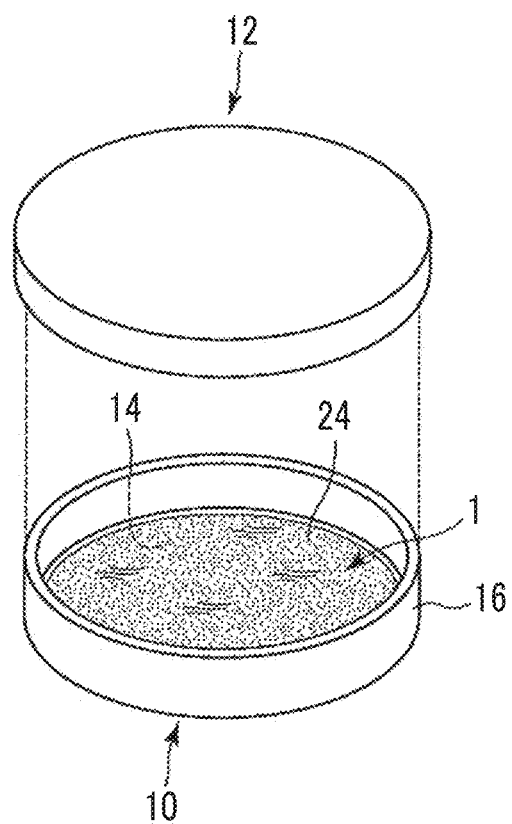
FIG. 1 is a perspective view of a culture container having a culture support body.

Hereinafter, an embodiment of the present invention will be described in detail.

A method for producing a sheet-like cell structure according to the present invention is a method including: a step of adding biocompatible macromolecular blocks, cells, and a liquid medium onto a culture support body having a plurality of recessed portions on a culture surface, and immersing the biocompatible macromolecular blocks and the cells in uppermost portions of the recessed portions; and a step of culturing the cells to obtain a sheet-like cell structure.

In the present invention, the culture is performed in a state of immersing the biocompatible macromolecular blocks and the cells in the uppermost portions of the plurality of recessed portions by adding the biocompatible macromolecular blocks, the cells, and the liquid medium onto the culture support body having the recessed portions on the culture surface. That is, it is necessary to use biocompatible macromolecular blocks and cells in an amount exceeding the uppermost portions of the recessed portions. As described above, it is possible to produce a sheet-like cell structure by performing the culture in a state where the biocompatible macromolecular blocks and the cells are immersed in the uppermost portions of the recessed portions. In a case where the amount of biocompatible macromolecular blocks and cells used are small and the culture is carried out in a state where the biocompatible macromolecular blocks and the cells are not immersed in the uppermost portions of the recessed portions, an individual cell structure is formed in an individual recessed portion. Therefore, it is impossible to form a sheet-like cell structure.

In a case where biocompatible macromolecular blocks and cells are cultured on a culture support body having no recessed portions on the culture surface, a brittle sheet-like cell structure is obtained. In the present invention, it has been found that, in a case where biocompatible macromolecular blocks and cells are cultured on a culture support body having a plurality of recessed portions on the culture surface, it is possible to produce a sheet-like cell structure having excellent strength and shape-maintaining performance (without rolling).

A culture support body having a plurality of recessed portions on the culture surface is disclosed in WO2012/036011A and JP2015-73520A. In WO2012/036011A and JP2015-73520A, it is disclosed that an individual spheroid is produced in an individual recessed portion (that is, one spheroid is produced per recessed portion) and a large number of spheroids are produced at the same time. However, there is no disclosure of producing a sheet-like cell structure by performing the culture in a state where the cells is immersed in the uppermost portions of the recessed portions. In addition, there is no disclosure of the use of biocompatible macromolecular blocks in WO2012/036011A and JP2015-73520A.

As shown in the examples and comparative examples to be described below in the present specification, in a case where only cells are used, it is possible to obtain a more favorable result from a case where a cell support body of which the surface is flat is produced compared to a case where a cell support body having recessed portions on the surface thereof is produced. In contrast, it has been found in the present invention that, in a case of producing a cell structure using cells and biocompatible macromolecular blocks, it is possible to obtain a more favorable result from the case where a cell support body having recessed portions on the surface thereof is produced compared to the case where a cell support body of which the surface is flat is produced.

According to the present invention, a sheet-like cell structure having excellent strength and shape-maintaining performance can be simply produced in a short period of time. However, completely opposite forms of preferred cell support bodies in the case of using only cells and in the case of using cells and biocompatible macromolecular blocks show that the effect of the present invention is completely unexpected.

The sheet-like cell structure produced through the method of the present invention contains biocompatible macromolecular blocks and cells. In the present specification, in some cases, the cell structure may be referred to as a mosaic cell aggregation (a cell aggregation having a mosaic shape).

(1) Culture Support Body

In the present invention, a culture support body having a plurality of recessed portions on a culture surface is used.

An example of the culture support body used in the present invention will be described with reference to FIGS. 1 to 6.

In FIG. 1, a culture support body 1 is a main part of a culture container for producing a sheet-like cell structure by culturing biocompatible macromolecular blocks and cells. As shown in FIG. 1, the culture container has a container main body 10 and a lid 12. In the example shown in FIG. 1, a bottom plate portion 14 on the inside of the container main body 10 is a portion corresponding to the culture support body 1. The bottom plate portion 14 on the inside of the container main body 10, that is, the culture support body 1 may be made of, for example, a synthetic resin material such as polystyrene, or glass. The culture support body 1 can be produced through injection molding using the synthetic resin material.

The container main body 10 has the disk-like bottom plate portion 14 and an annular side wall portion 16.

The shape of the container may be a shape other than a disk shape or a shape such as a square. The side wall portion 16 rises from an outer peripheral edge of the bottom plate portion 14. The diameter of the bottom plate portion 14 can be set, for example, to 30 mm to 500 mm, the thickness of the bottom plate portion 14 can be set, for example, to 0.5 mm to 10 mm, and the height of the side wall portion 16 can be set, for example, to 20 mm to 100 mm, but are not particularly limited.

The lid 12 is formed in a shape corresponding to an upper opening portion in the container main body 10.

The lid 12 can be used by covering the container main body 10 in order to maintain the culture environment of cells.

A plurality of recessed portions 20 are formed in a well formation region 24 (that is, a region where compartments in which an object to be cultured is cultured are formed) on the upper surface of the bottom plate portion 14 (that is, the upper surface of a culture support body corresponding to the inner surface of the container main body 10) as shown in FIGS. 2A and 2B or FIGS. 3A and 3B.

The inner surfaces of the recessed portions 20 are smooth concave surfaces. The recessed portions 20 form compartments (wells) in which an object to be cultured is cultured.

Figure 2A:
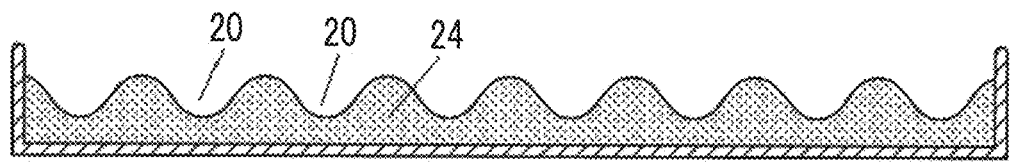
FIGS. 2A and 2B are a cross-sectional view of a first example of a culture support body (of which the surfaces between recessed portions are non-flat).
Figure 2B:
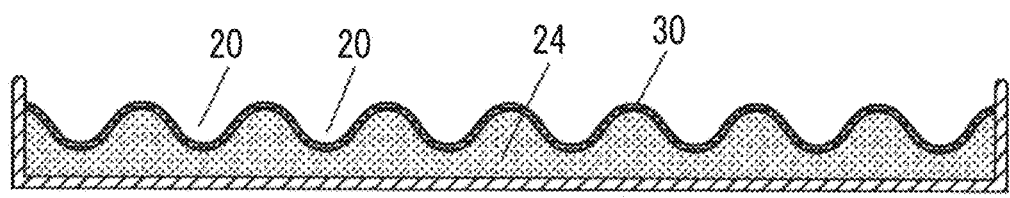
Figure 3A:
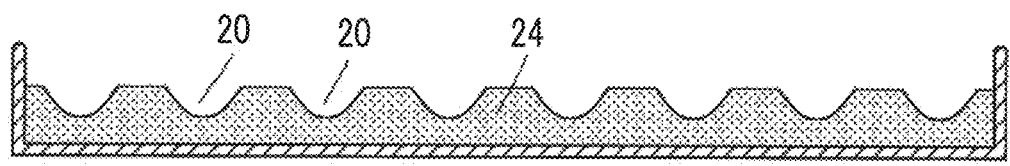
FIGS. 3A and 3B are a cross-sectional view of a second example of a culture support body (of which the surfaces between recessed portions are flat).
Figure 3B:
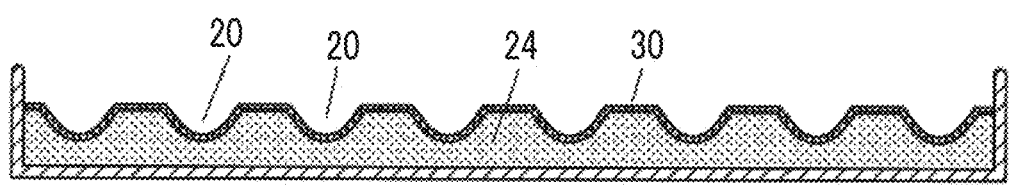

In the examples shown in FIGS. 2A and 3A, there is no cell adhesion suppressant layer. In the examples shown in FIGS. 2B and 3B, a cell adhesion suppressant layer 30 is provided.

The depths of the recessed portions are not particularly limited, but are preferably 10 to 2,000 μm, more preferably 20 to 1,000 μm, still more preferably 30 to 700 μm, still more preferably 50 to 500 μm, and most preferably 100 to 400 μm.

The diameters of the recessed portions are not particularly limited, but are preferably 10 to 2,000 μm, more preferably 50 to 1,500 μm, still more preferably 100 to 1,500 μm, still more preferably 200 to 1,000 μm, and most preferably 400 to 800 μm.

The setting of the depths and the diameters of the recessed portions to be within the above-described range is preferable from the viewpoint of obtaining a sheet-like cell structure having excellent strength and shape-maintaining performance in relation to the sizes of cells.

In a case where the recessed portions have the above-described depths and diameters, it is not necessary for all the recessed portions on the culture support body to have the above-described depths and diameters, and at least some recessed portions may have the above-described depths and diameters.

Figure 4:
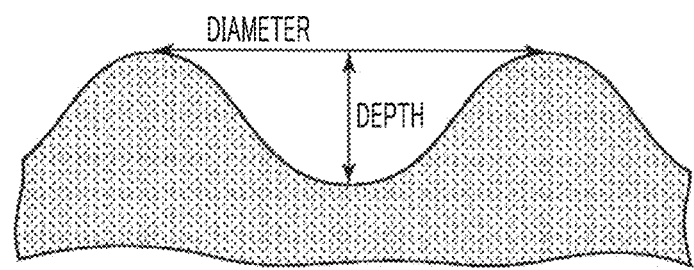
FIG. 4 is a partially enlarged view of FIG. 2A.
Figure 5:
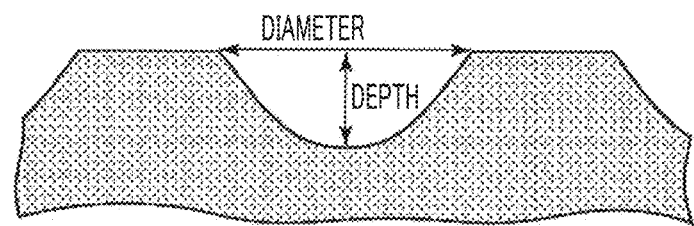
FIG. 5 is a partially enlarged view of FIG. 3A.

As shown in FIGS. 4 and 5, the depth of a recessed portion means the height between the lowermost portion and the uppermost portion of the recessed portion. As shown in FIGS. 4 and 5, the diameter of a recessed portion means the length connecting points of uppermost portions of the recessed portions. As shown in FIG. 5, in a case where the uppermost portions of the recessed portions are flat, the uppermost portions of recessed portions are selected so that the length connecting points of the uppermost portions of the recessed portions become the shortest.

The shapes (including the depths and the diameters) of the recessed portions may be uniform or nonuniform, but are preferably uniform. It is preferable that the depths and diameters of the recessed portions are uniform, and it is preferable that the depths and diameters of all the recessed portions are substantially the same.

The recessed portions 20 can be formed through, for example, irradiating the well formation region 24 on the surface of the culture support body with a laser light.

Figure 6:
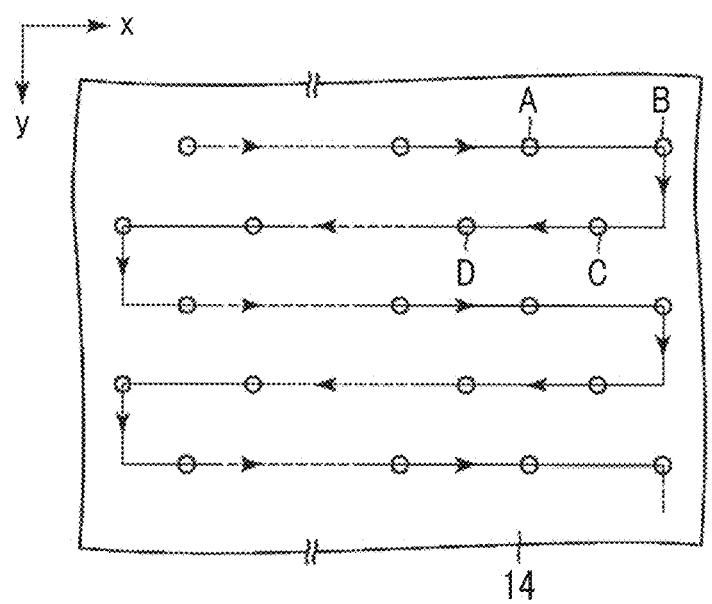
FIG. 6 shows spots on the surface of a culture support body irradiated with laser light.

As shown in FIG. 6, laser irradiation is performed by irradiating the upper surface of the bottom plate portion 14 installed on the x-y plane with laser light in the z-axis direction.

First, a plurality of recessed portions 20 arranged in the x-axis direction are formed by emitting laser light at regular intervals (for example, 800 µm) while making an irradiation portion of a laser irradiation device to perform scanning in the positive direction of the x-axis.

Subsequently, a plurality of recessed portions 20 arranged in the x-axis direction are formed by emitting laser light at regular intervals (for example, 800 µm) while the irradiation portion is made to perform scanning in the negative direction of the x-axis after the irradiation portion is made to perform scanning by a certain distance (for example, 400 µm) in the y-axis direction. Similarly, the irradiation portion is made to perform scanning by a certain distance (for example, 400 µm) in the y-axis direction. A plurality of recessed portions 20 regularly arranged on the upper surface of the bottom plate portion 14 are formed by repeating this process.

As shown in FIG. 6, in a case where the center coordinate (x, y) of an irradiation spot A is set to be an origin (0, 0), the center of an irradiation spot B close to the irradiation spot A is located at (0.8, 0), the center of an irradiation spot C is located at (0.4, 0.4), and the center of an irradiation spot D is located at (−0.4, 0.4). By shifting the x coordinate of the irradiation spots A and B and the x coordinate of the irradiation spots C and D in this manner, it is possible to densely form a plurality of recessed portions 20 in the well formation region 24. The recessed portions 20 are preferably formed in a range of $10/cm^2$ to $10,000/cm^2$ per unit area of the well formation region 24 of a culture support body 1. The range is more preferably $20/cm^2$ to $8,000/cm^2$, still more preferably $20/cm^2$ to $3,000/cm^2$, still more preferably $50/cm^2$ to $1,000/cm^2$, still more preferably $100/cm^2$ to $500/cm^2$, and particularly preferably $100/cm^2$ to $300/cm^2$.

A $CO_2$ laser is used as a laser light source. The laser light for pulse irradiation can be emitted at an output of 10 W and an irradiation speed of 6,100 mm/min, but is not particularly limited.

Although the shapes of the irradiation spots are circular, the opening shapes of the recessed portions 20 are flattened in a substantially elliptical shape. It is considered that the flatness of the opening shapes is caused by the direction in which the synthetic resin material is poured into a metal mold during molding of the container main body 10.

In a case where the surface of the culture support body (the upper surface of the bottom plate portion 14) is irradiated with laser light, the synthetic resin material forming the bottom plate portion 14 is melted and the recessed portions 20 are formed.

By adjusting the irradiation conditions such as the irradiation position and the output amount of the laser light, the distance between adjacent recessed portions 20, the diameters and depths of the recessed portions 20, the width and the height of the surface of the culture support body between the recessed portions 20 adjacent to each other, and the like can be adjusted.

The culture support body 1 can be produced by subjecting a synthetic resin material to injection molding using a mold which has convex portions forming the plurality of recessed portions 20 and concave portions forming the surface of the culture support body between the recessed portions. The plurality of recessed portions 20 and the surface of the culture support body between the plurality of recessed portions is formed simultaneously with the molding of the culture support body 1. By producing the culture support body 1 through injection molding using a mold, it is possible to form the recessed portions 20 having higher uniformity.

The area of the recessed portions on the culture surface is preferably greater than or equal to 70%, more preferably greater than or equal to 80%, still more preferably greater than or equal to 90%, and most preferably 100% with respect to the whole area of the culture surface. It is preferable to set the ratio of the area of the recessed portions to be within the above-described range from the viewpoint of the effect of the present invention.

The area of the recessed portions means the area in a case where the recessed portions are two-dimensionally caught in a case where the recessed portions are observed from above, and means the area of the region defined by the diameter of the recessed portion described above in the present specification. As shown in FIG. 2A or 2B or FIG. 4, in a case where there is no flat portion on the culture surface, the area of the recessed portions on the culture surface becomes 100% with respect to the whole area of the culture surface.

Two mutually adjacent recessed portions 20 are formed through the surface of the culture support body between the recessed portions. The surface of the culture support body between the mutually adjacent recessed portions 20 may be flat or non-flat, but is preferably non-flat.

It is preferable that the upper surface of the bottom plate portion 14, that is, the culture surface of the culture support body is subjected to a treatment for suppressing adhesion of cells. Accordingly, it is possible to facilitate peeling after culturing the sheet-like cell structure. Examples of the treatment for suppressing adhesion of cells include coating using a cell adhesion suppressant (refer to FIGS. 2B and 3B). The cell adhesion suppressant plays a role of suppressing adhesion of cells to the upper surface of the bottom plate portion 14, particularly to the inner surfaces of the recessed portions 20. For example, a phospholipid polymer, 2-methacryloyloxyethyl phosphorylcholine (MPC), polyhydroxyethyl methacrylate, polyethylene glycol, or the like is used as the cell adhesion inhibitor.

(2) Biocompatible Macromolecular Block (2-1) Biocompatible Macromolecules

Biocompatibility means a property which does not cause a significantly harmful reaction such as a long-term and chronic inflammatory reaction, during contact with a living body. Whether or not the biocompatible macromolecules used in the present invention are decomposed within a living body is not particularly limited as long as the biocompatible macromolecules have affinity to the living body. However, biodegradable macromolecules are preferable. Specific examples of non-biodegradable materials include polytetrafluoroethylene (PTFE), polyurethane, polypropylene, polyester, vinyl chloride, polycarbonate, acryl, stainless steel, titanium, silicone, and 2-methacryloyloxyethyl phosphorylcholine (MPC). Specific examples of the biodegradable materials include naturally derived peptides, polypeptides (for example, gelatin or the like to be described below) such as a recombinant peptide or a chemically synthesized peptide, polylactic acid, polyglycolic acid, lactic acid-glycolic acid copolymers (PLGA), hyaluronic acid, glycosaminoglycan, proteoglycan, chondroitin, cellulose, agarose, carboxymethyl cellulose, chitin, and chitosan. Among these, a recombinant peptide is particularly preferable. Devising of an improvement of cell adhesion properties in these biocompatible macromolecules may be performed. Specifically, methods such as "coating of the surface of a base material with a cell adhesion substrate (fibronectin, vitronectin, or laminin) or peptides of a cell adhesion sequence (an RGD sequence, an LDV sequence, an REDV sequence (SEQ ID NO: 2), a YIGSR sequence (SEQ ID NO: 3), a PDSGR sequence (SEQ ID NO: 4), an RYVVLPR sequence (SEQ ID NO: 5), an LGTIPG sequence (SEQ ID NO: 6), an RNIAEIIKDI sequence (SEQ ID NO: 7), an IKVAV sequence (SEQ ID NO: 8), an LRE sequence, a DGEA sequence (SEQ ID NO: 9), and a HAV sequence, which are represented by one-letter notation of amino acids)", "amination or cationization of the surface of a base material", or "plasma treatment performed on the surface of a base material or hydrophilic treatment due to corona discharge" can be used.

The kind of polypeptide containing a recombinant peptide or a chemically synthesized peptide is not particularly limited as long as a polypeptide has biocompatibility. For example, gelatin, collagen, elastin, fibronectin, ProNectin, laminin, tenascin, fibrin, fibroin, entactin, thrombospondin, and RetroNectin are preferable and gelatin, collagen, and atelocollagen are most preferable. As the gelatin to be used in the present invention, natural gelatin, recombinant gelatin, or chemically synthesized gelatin is preferable and recombinant gelatin is more preferable. The natural gelatin referred to herein means gelatin produced using naturally derived collagen.

The chemically synthesized peptide or the chemically synthesized gelatin means an artificially synthesized peptide or gelatin. The synthesis of a peptide such as gelatin may be solid phase synthesis or liquid phase synthesis, but is preferably solid phase synthesis. The solid phase synthesis of a peptide is well-known to those skilled in the art, and examples thereof include a fluorenyl-methoxy-carbonyl group (Fmoc group) synthesis method in which a Fmoc group is used for protection of an amino group, and a tert-butyl oxy carbonyl group (Boc group) synthesis method in which a Boc group is used for protection of an amino group. As a preferred embodiment of the chemically synthesized gelatin, it is possible to apply the contents in (2-3) Recombinant Gelatin to be described below in the present specification.

The recombinant gelatin will be described below in the present specification.

A "1/IOB" value which is a hydrophilic value of biocompatible macromolecules used in the present invention is preferably within a range of 0 to 1.0, more preferably within a range of 0 to 0.6, and still more preferably within a range of 0 to 0.4. IOB is an index of hydrophilic and hydrophobic properties based on an organic conceptual diagram representing polarity and non-polarity of an organic compound proposed by Atsushi HUJITA, and the details thereof are described in, for example, "Pharmaceutical Bulletin", vol. 2, 2, pp. 163-173 (1954), "Area of Chemistry" vol. 11, 10, pp. 719-725 (1957), and "Fragrance Journal, vol. 50, pp. 79-82 (1981). Briefly, the root of every organic compound is set to methane ($CH_4$), and all of other compounds are regarded as derivatives of methane. Certain numerical values for the number of carbons thereof, a substituent group, a transformation portion, a ring, and the like are set, and an organic value (OV) and an inorganic value (IV) are obtained by adding the score thereof. These values are plotted on a diagram in which the organic value is shown on the X-axis and the inorganic value is shown on the Y-axis. IOB in the organic conceptual diagram refers to a ratio of the inorganic value (IV) to the organic value (OV) in the organic conceptual diagram, that is, "inorganic value (IV)/organic value (OV)". The details of the organic conceptual diagram can be referred to "New Edition Organic Conceptual Diagram-Foundation and Application-" (written by Yoshio KOUDA, Sankyo Shuppan Co., Ltd., 2008). In the present specification, the hydrophilic and hydrophobic properties are represented by a "1/IOB" value which was obtained by taking a reciprocal number of IOB. This is a notation of representing more hydrophilic properties as the "1/IOB" value becomes small (close to 0).

The hydrophilic properties and water absorbency become high by making the "1/IOB" value of the macromolecules used in the present invention be within the above-described range, which effectively acts to hold nutrient components.

In a case where the biocompatible macromolecules used in the present invention are polypeptides, the hydrophilic and hydrophobic indexes represented by a grand average of hydropathicity (GRAVY) value is preferably −9.0 to 0.3, and more preferably −7.0 to 0.0. The grand average of hydropathicity (GRAVY) value can be obtained through "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appeal R. D., Bairoch A.; ExPASy: the proteomics server for in-depth protein knowledge and analysis.; Nucleic Acids Res. 31:3784-3788 (2003)".

The hydrophilic properties and water absorbency become high by making the GRAVY value of the macromolecules used in the present invention be within the above-described range, which effectively acts to hold nutrient components.

(2-2) Cross-Linking

The biocompatible macromolecules used in the present invention may be or may not be cross-linked, but are preferably cross-linked. By using the cross-linked biocompatible macromolecules, it is possible to obtain an effect of preventing instant decomposition during culturing in a medium and during transplantation into a living body. As general cross-linking methods, thermal cross-linking, cross-linking using aldehydes (for example, formaldehyde or glutaraldehyde), cross-linking using a condensation agent (carbodiimide, cyanamide, or the like), enzymatic cross-linking, photocrosslinking, ultraviolet cross-linking, a hydrophobic interaction, hydrogen bonding, an ionic interaction, and the like are known, it is also possible to use the above-described cross-linking methods in the present invention. As the cross-linking methods used in the present invention, thermal cross-linking, ultraviolet cross-linking, or enzymatic cross-linking is more preferable, and thermal cross-linking is particularly preferable.

In a case of performing cross-linking using an enzyme, there is no particular limitation as long as the enzyme has a cross-linking action between macromolecular materials. However, it is possible to perform cross-linking preferably using transglutaminase and laccase and most preferably using transglutaminase. Specific examples of protein to be subjected to enzymatic cross-linking using transglutaminase are not particularly limited as long as the protein has a lysine residue and a glutamine residue. Transglutaminase may be derived from a mammal or may be derived from a microorganism. Specific examples thereof include mammal-derived transglutaminase which has been sold as Activa series manufactured by Ajinomoto Co., Inc., and a reagent; guinea pig liver-derived transglutaminase manufactured by, for example, Oriental Yeast Co., Ltd., Upstate USA Inc., or Biodesign International, Inc.; goat-derived transglutaminase; rabbit-derived transglutaminase; and human-derived blood coagulation factors (Factor XIIIa: Haematologic Technologies, Inc).

The reaction temperature in a case of performing cross-linking (for example, thermal cross-linking) is not particularly limited as long as cross-linking can be performed, but is preferably −100° C. to 500° C., more preferably 0° C. to 300° C., still more preferably 50° C. to 300° C., still more preferably 100° C. to 250° C., and still more preferably 120° C. to 200° C.

(2-3) Recombinant Gelatin

The recombinant gelatin referred in the present invention means polypeptides or protein-like substances which have an amino acid sequence similar to that of gelatin produced through gene recombination technology. The recombinant gelatin which can be used in the present invention preferably has a repetition of a sequence (X and Y each independently show any amino acids) represented by Gly-X-Y which is characteristic to collagen. Here, a plurality of pieces of Gly-X-Y may be the same as or different from each other. Preferably, two or more sequences of cell adhesion signals are included in one molecule As the recombinant gelatin used in the present invention, it is possible to use recombinant gelatin having an amino acid sequence derived from a partial amino acid sequence of collagen, and to use recombinant gelatin disclosed in, for example, EP1014176A2, U.S. Pat. No. 6,992,172B, WO2004/85473A, and WO2008/103041A. However, the recombinant gelatin is not limited thereto. Preferred recombinant gelatin used in the present invention is recombinant gelatin of the following aspect.

The recombinant gelatin is excellent in biocompatibility with original performance of natural gelatin, and is excellent in non-infection properties since there is no concern of bovine spongiform encephalopathy (BSE) and the recombinant gelatin with not being naturally derived. In addition, the recombinant gelatin is even compared to natural gelatin, and a sequence is determined. Therefore, it is possible to accurately design the strength and degradability so as to reduce deviation through cross-linking or the like.

The molecular weight of recombinant gelatin is not particularly limited, but is preferably 2,000 to 100,000 (2 kDa to 100 kDa), more preferably (2,500 to 95,000 (2.5 kDa to 95 kDa), still more preferably 5,000 to 90,000 (5 kDa to 90 kDa), and most preferably 10,000 to 90,000 (10 kDa to 90 kDa).

The recombinant gelatin preferably has a repetition of a sequence represented by Gly-X-Y which is characteristic to collagen. Here, a plurality of pieces of Gly-X-Y may be the same as or different from each other. In Gly-X-Y, Gly represents glycine and X and Y represent an arbitrary amino acid (preferably represents an arbitrary amino acid other than glycine). The sequence represented by Gly-X-Y characteristic to collagen is a partial structure which is extremely specific compared to other protein in a composition or a sequence of an amino acid of gelatin/collagen. In this section, glycine occupies about one third of the entirety of the amino acid sequence, one sequence is repeated every three sequences. Glycine is the simplest amino acid. Therefore, there is a little restraint in arrangement of molecular chains and glycine significantly contributes to regeneration of a helix structure during gelation. It is preferable that amino acids represented by X and Y contain many imino acids (proline and oxyproline) and occupy 10% to 45% of the entirety of the sequence. Preferably 80% or more of the sequence of the amino acids, more preferably 95% or more of the sequence of the amino acids, and most preferably 99% or more of the sequence of the amino acids in the recombinant gelatin has a repeating structure of Gly-X-Y.

In general gelatin, a polar amino acid with an electrical charge and a polar non-charged amino acid exist by 1:1 in polar amino acids. Here, the polar amino acid specifically indicates cysteine, aspartic acid, glutamic acid, histidine, lysine, asparagine, glutamine, serine, threonine, tyrosine, or arginine. Among these, the polar non-charged amino acid indicates cysteine, asparagine, glutamine, serine, threonine, or tyrosine. In recombinant gelatin used in the present invention, the proportion of the polar amino acid in the whole constituent amino acid is 10% to 40% and preferably 20% to 30%. It is preferable that the proportion of a non-charged amino acid in the polar amino acid is greater than or equal to 5% and less than 20% and preferably less than 10%. Furthermore, it is preferable that any one amino acid or preferably two or more amino acids among serine, threonine, asparagine, tyrosine, and cysteine are not contained on a sequence.

In general, in polypeptides, minimum amino acid sequences which work as cell adhesion signals are known (for example, Nagai Shoten Co., Ltd., "Pathophysiology", Vol. 9, No. 7 (1990) p. 527). The recombinant gelatin used in the present invention preferably has two or more these cell adhesion signals in one molecule. As the specific sequences, sequences such as an RGD sequence, an LDV sequence, an REDV sequence (SEQ ID NO: 2), a YIGSR sequence (SEQ ID NO: 3), a PDSGR sequence (SEQ ID NO: 4), an RYVVLPR sequence (SEQ ID NO: 5), an LGTIPG sequence (SEQ ID NO: 6), an RNIAEIIKDI sequence (SEQ ID NO: 7), an IKVAV sequence (SEQ ID NO: 8), an LRE sequence, a DGEA sequence (SEQ ID NO: 9), and a HAV sequence, which are represented by one-letter notation of amino acids are preferable in that there are many kinds of cells adhered. An RGD sequence, a YIGSR sequence (SEQ ID NO: 3), a PDSGR sequence (SEQ ID NO: 4), an LGTIPG sequence (SEQ ID NO: 6), an IKVAV sequence (SEQ ID NO: 8), and a HAV sequence are more preferable and an RGD sequence is particularly preferable. In the RGD sequence, an ERGD sequence (SEQ ID NO: 10) is preferable. It is possible to improve the production amount of substrate of a cell using recombinant gelatin having cell adhesion signals. For example, it is possible to improve the production of glycosaminoglycan (GAG) in a case of cartilage differentiation using mesenchymal stem cells as cells.

As arrangement of RGD sequences in recombinant gelatin used in the present invention, it is preferable that the number of amino acids between RGDs is between 0 to 100 and preferably between 25 to 60 without being even.

The content of this minimum amino acid sequence is preferably 3 to 50, more preferably 4 to 30, and particularly preferably 5 to 20 in one molecule of protein in view of cell adhesion properties and proliferation properties. The most preferable content thereof is 12.

In recombinant gelatin used in the present invention, the proportion of RGD motifs with respect to the total number of amino acids is preferably at least 0.4%. In a case where recombinant gelatin contains 350 or more amino acids, each stretch of the 350 amino acids preferably contains at least one RGD motif. The proportion of RGD motifs with respect to the total number of amino acids is still more preferably at least 0.6%, still more preferably at least 0.8%, still more preferably at least 1.0%, still more preferably at least 1.2%, and most preferably at least 1.5%. The number of RGD motifs within a recombinant peptides is, per 250 amino acids, preferably at least 4, still more preferably 6, still more preferably 8, and still more preferably 12 to 16. The proportion of RGD motifs being 0.4% corresponds to at least one RGD sequence per 250 amino acids. The number of RGD motifs is an integer, and therefore, gelatin formed of 251 amino acids needs to contain at least two RGD sequences in order to satisfy the characteristics of 0.4%. It is preferable that the recombinant gelatin of the present invention contains at least two RGD sequences per 250 amino acids, more preferably contains at least three RGD sequences per 250 amino acids, and still more preferably contains at least four RGD sequences per 250 amino acids. As a further mode of the recombinant gelatin of the present invention, the recombinant gelatin contains at least 4 RGD motifs, preferably 6 RGD motifs, more preferably 8 RGD motifs, and still more preferably 12 to 16 RGD motifs.

In addition, the recombinant gelatin may be partially hydrolyzed.

The recombinant gelatin used in the present invention is preferably represented by Formula 1: A-[(Gly-X-Y)$_n$]$_m$-B. n pieces of X each independently represent any amino acid and n pieces of Y each independently represent any amino acid. m preferably represents an integer of 2 to 10 and more preferably represents an integer of 3 to 5. n is preferably an integer of 3 to 100, more preferably an integer of 15 to 70, and most preferably an integer of 50 to 65. A represents an arbitrary amino acid or an amino acid sequence, B represents an arbitrary amino acid or an amino acid sequence. n pieces of Gly-X-Y may be the same as or different from each other.

More preferably, the recombinant gelatin used in the present invention is represented by Formula: Gly-Ala-Pro-[(Gly-X-Y)63]3-Gly (SEQ ID NO: 11) (in the formula, 63 pieces of X (=Xaa) each independently represent any amino acid and 63 pieces of Y (=Xaa) each independently represent any amino acid. 63 pieces of Gly-X-Y may be the same as or different from each other).

It is preferable that a plurality of sequence units of collagen which naturally exists are bonded to a repeating unit. Any naturally existing collagen referred to herein may be used as long as the collagen naturally exists, but is preferably I type collagen, II type collagen, III type collagen, IV type collagen, or V type collagen, and more preferably I type collagen, II type collagen, or III type collagen. According to another form, the above-described collagen is preferably derived from a human, cattle, a pig, a mouse, or a rat, and is more preferably derived from a human.

An isoelectric point of the recombinant gelatin used in the present invention is preferably 5 to 10, more preferably 6 to 10, and still more preferably 7 to 9.5. The measurement of the isoelectric point of the recombinant gelatin can be carried out by measuring the pH after passing a 1 mass % gelatin solution through a mixed crystal column of a cation-anion exchange resin above-described disclosed in isoelec-tric focusing method (refer to Maxey, C. R. (1976; Phitogr. Gelatin 2, Editor Cox, P. J. Academic, London, Engl.)).

It is preferable that the recombinant gelatin is not deaminated.

It is preferable that the recombinant gelatin does not have a telopeptide.

It is preferable that the recombinant gelatin is a substantially pure polypeptide which is prepared using a nucleic acid encoding an amino acid sequence.

It is particularly preferable that the recombinant gelatin used in the present invention is any of
(1) a peptide formed of an amino acid sequence described in SEQ ID No: 1;
(2) a peptide which is formed of an amino acid sequence in which one or several amino acids are deleted, substituted, or added in the amino acid sequence described in SEQ ID No: 1, and has biocompatibility; or
(3) a peptide which is formed of an amino acid sequence having 80% or more (more preferably 90% or more, particularly preferably 95% or more, and most preferably 98% or more) sequence identity to the amino acid sequence described in SEQ ID No: 1, and has biocompatibility.

"One or several" in the "amino acid sequence in which one or several amino acids are deleted, substituted, or added" preferably means 1 to 20 amino acids, more preferably means 1 to 10 amino acids, still more preferably means 1 to 5 amino acids, and particularly preferably means 1 to 3 amino acids.

The recombinant gelatin used in the present invention can be produced through gene recombination technology which is known to those skilled in the art, and can be produced in accordance with, for example, methods disclosed in EP1014176A2, U.S. Pat. No. 6,992,172B, WO2004/85473A, and WO2008/103041A. Specifically, a gene encoding an amino acid sequence of predetermined recombinant gelatin is acquired, the acquired gene is incorporated into an expression vector to produce a recombinant expression vector, and a transformant is produced by introducing the recombinant expression vector into an appropriate host. The recombinant gelatin is produced by culturing the obtained transformant in an appropriate medium. Therefore, it is possible to prepare the recombinant gelatin used in the present invention by collecting the recombinant gelatin produced from a culture product.

(2-4) Biocompatible Macromolecular Block

In the present invention, a block (aggregation) formed of the above-described biocompatible macromolecules is used.

The shape of the biocompatible macromolecular block in the present invention is not particularly limited. Examples thereof include an amorphous shape, a spherical shape, a particulate shape (granule), a powdery shape, a porous shape, a fibrous shape, a spindle shape, a flat shape, and a sheet shape. An amorphous shape, a spherical shape, a particulate shape (granule), a powdery shape, and a porous shape are preferable. The amorphous shape indicates that the shape of a surface is uneven, and indicates, for example, an object, such as rock, which has roughness. Examples of the above-described shapes are not distinct from each other. For example, in some cases, an example of a subordinate concept of the particulate shape (granule) is an amorphous shape.

The shape of the biocompatible macromolecular block in the present invention is not particularly limited as described above. However, the tap density is preferably 10 mg/cm$^3$ to 500 mg/cm$^3$, more preferably 20 mg/cm$^3$ to 400 mg/cm$^3$, still more preferably 40 mg/cm$^3$ to 220 mg/cm$^3$, and particularly preferably 50 mg/cm$^3$ to 150 mg/cm$^3$.

The tap density is a value indicating how much volume of block can be densely filled. It can be seen that, as the value becomes smaller, the block cannot be densely filled, that is, the structure of the block is complicated. It is considered that the tap density of the biocompatible macromolecular block indicates the complexity of a surface structure of the biocompatible macromolecular block and the amount of void formed in a case where biocompatible macromolecular blocks are collected as an aggregate. As the tap density becomes smaller, the void between biocompatible macromolecular blocks becomes larger and a grafted region of a cell becomes larger. In addition, in a case where the tap density is not too small, the biocompatible macromolecular block can appropriately exist between cells and nutrients can be delivered into a cell structure in a case where the cell structure is produced, and therefore, it is considered that it is preferable that the tap density falls within the above-described range.

The tap density referred to in the present specification can be measured as follows. A container (with a cylindrical shape with a diameter of 6 mm and a length of 21.8 mm: a capacity of 0.616 cm$^3$) (hereinafter, described as a cap) is prepared for the measurement of the tap density. First, the mass of only a cap is measured Thereafter, a funnel is attached to the cap, and blocks are poured from the funnel so as to be collected in the cap. After placing a sufficient amount of block, the cap portion is hit 200 times on a hard object such as a desk, the funnel is removed, and the blocks are leveled with a spatula. The mass is measured in a state where the cap is filled up with the blocks. The tap density can be obtained by calculating the mass of only the blocks from the difference between the mass of the cap filled up with the blocks and the mass of only the cap, and dividing the mass of only the blocks by the volume of the cap.

The cross-linking degree of the biocompatible macromolecular block in the present invention is not particularly limited, but is preferably greater than or equal to 2, more preferably 2 to 30, still more preferably 4 to 25, and particularly preferably 4 to 22.

The method for measuring the solid (the number of cross-linking times per molecule) of a biocompatible macromolecular block is not particularly limited. However, the cross-linking degree can be measured, for example, through a TNBS (2,4,6-trinitrobenzene sulfonic acid) method in examples to be described below. Specifically, a sample obtained by mixing biocompatible macromolecular blocks, a NaHCO$_3$ aqueous solution, and a TNBS aqueous solution, allowing the mixture to react for 3 hours at 37° C., and then, stopping the reaction, and a blank obtained by mixing biocompatible macromolecular blocks, a NaHCO$_3$ aqueous solution, and a TNBS aqueous solution and stopping a reaction immediately after the mixing were prepared. The cross-linking degree (the number of cross-linking times per molecule) can be calculated from (Formula 2) and (Formula 3) by measuring each absorbance (345 nm) of the sample and the blank which have been diluted with pure water.

$(As-Ab)/14,600 \times V/w$ (Formula 2)

(Formula 2) represents the amount (molar equivalent) of lysine per 1 g of biocompatible macromolecular blocks.
(in the formula, As represents the sample absorbance, Ab represents the blank absorbance, V represents the amount (g) reaction liquid, and w represents the mass (mg) of the biocompatible macromolecular blocks.)

$1-(\text{sample}(\text{Formula 2})/\text{uncross-linked macromolecules}(\text{Formula 2})) \times 34$ (Formula 3)

(Formula 3) represents the number of cross-linking times per molecule.

The water absorption rate of the biocompatible macromolecular block in the present invention is not particularly limited, but is preferably greater than or equal to 300%, more preferably greater than or equal to 400%, still more preferably greater than or equal to 500%, particularly preferably greater than or equal to 700%, and most preferably greater than or equal to 800%. The upper limit of the water absorption rate is not particularly limited, but is generally less than or equal to 4,000% or less than or equal to 2,000%.

The method for measuring the water absorption rate of the biocompatible macromolecular block is not particularly limited. However, the water absorption rate of the biocompatible macromolecular block can be measured, for example, through the method in examples to be described below. Specifically, a 3 cm×3 cm nylon mesh bag is filled with about 15 mg of biocompatible macromolecular blocks at 25° C. and is swollen in ion exchange water for 2 hours. Then, the biocompatible macromolecular blocks are dried with air for 10 minutes, and the mass is measured at each stage to obtain the water absorption rate according to (Formula 4).

Water absorption rate$=(w2-w1-w0)/w0$ (Formula 4)

(in the formula, w0 represents the mass of a material before water absorption, w1 represents the mass of an empty bag after water absorption, and w2 represents the mass of the entirety of the bag containing the material after water absorption.)

The size of one biocompatible macromolecular block in the present invention is not particularly limited, but is preferably 1 μm to 700 μm, more preferably 10 μm to 700 μm, still more preferably 10 μm to 300 μm, still more preferably 20 μm to 200 μm, still more preferably 20 μm to 150 μm, and particularly preferably 53 μm to 106 μm. It is possible to favorably deliver nutrients into a cell structure from the outside by setting the size of one biocompatible macromolecular block to be within the above-described range. The size of one biocompatible macromolecular block does not mean that an average value of the sizes of a plurality of biocompatible macromolecular blocks is within the above-described range, but means the size of each biocompatible macromolecular block which is obtained by sieving a plurality of biocompatible macromolecular blocks.

The size of one block can be defined by the size of a sieve used in a case of dividing the block. For example, blocks remaining on a sieve with 106 μm in a case where blocks which have been passed through a sieve with 180 μm for sifting are sifted using the sieve with 106 μm can be regarded as blocks having a size of 106 to 180 μm. Next, blocks remaining on a sieve with 53 μm in a case where blocks which have been passed through the sieve with 106 μm for sifting are sifted using the sieve with 53 μm can be regarded as blocks having a size of 53 to 106 μm. Next, blocks remaining on a sieve with 25 μm in a case where blocks which have been passed through the sieve with 53 μm for sifting are sifted using the sieve with 25 μm can be regarded as blocks having a size of 25 to 53 μm.

(2-5) Method for Producing Biocompatible Macromolecular Block

The method for producing a biocompatible macromolecular block is not particularly limited. For example, it is possible to obtain a biocompatible macromolecular block by pulverizing a solid matter (such as a porous body of a biocompatible macromolecule) containing a biocompatible macromolecule using a pulverizer (such as NEW POWER-MILL). The solid matter (such as a porous body of a biocompatible macromolecule) containing a biocompatible macromolecule can be obtained, for example, by freeze-drying an aqueous solution containing the biocompatible macromolecule.

It is possible to produce an amorphous biocompatible macromolecular block of which the shape of the surface is uneven, by pulverizing a solid matter containing a biocompatible macromolecule as described above.

An example of the method for producing a porous body of a biocompatible macromolecule include a method including (a) a step of cooling a solution of biocompatible macromolecules under the conditions where the difference between the temperature of a portion having the highest liquid temperature within the solution and the temperature of a portion having the lowest liquid temperature within the solution is lower than or equal to 2.5° C. and the temperature of a portion having the highest liquid temperature within the solution is lower than or equal to a melting point, to an unfrozen state, (b) a step of freezing the solution of the biocompatible macromolecules obtained in the step (a), and (c) a step of freeze-drying the frozen biocompatible macromolecules obtained in the step (b)

In a case where the solution of the biocompatible macromolecules is cooled to an unfrozen state, the variation in the size of pores of an obtained porous body is reduced by making the difference between the temperature of a portion having the highest liquid temperature and the temperature of a portion having the lowest liquid temperature within the solution be lower than or equal to 2.5° C. (preferably lower than or equal to 2.3° C. and more preferably lower than or equal to 2.1° C.), that is, by reducing the difference in temperature. The lower limit of the difference between the temperature of a portion having the highest liquid temperature and the temperature of a portion having the lowest liquid temperature within the solution is not particularly limited, but may be higher than or equal to 0° C. For example, the lower limit thereof may be higher than or equal to 0.1° C., higher than or equal to 0.5° C., higher than or equal to 0.8° C., or higher than or equal to 0.9° C.

The cooling in the step (a) is preferably carried out, for example, using a material (preferably TEFLON (registered trademark)) having a lower thermal conductivity than water. The portion having the highest liquid temperature within the solution can be supposed as the farthest portion from a cooling side, and the portion having the lowest liquid temperature within the solution can be supposed as a liquid temperature of the cooling surface.

In the step (a), the difference between the temperature of a portion having the highest liquid temperature within the solution and the temperature of a portion having the lowest liquid temperature within the solution immediately before generation of solidification heat is preferably lower than or equal to 2.5° C., more preferably lower than or equal to 2.3° C., and still more preferably lower than or equal to 2.1° C. Here, the "difference in temperature immediately before the generation of solidification heat" means a difference in temperature in a case where the difference in temperature becomes largest between 1 second and 10 seconds before the generation of solidification heat.

In the step (a), the temperature of a portion having the lowest liquid temperature within the solution is preferably lower than or equal to a melting point of a solvent −5° C., more preferably lower than or equal to a melting point of a solvent −5° C. and higher than or equal to a melting point of a solvent −20° C., and still more preferably lower than or equal to a melting point of a solvent −6° C. and higher than or equal to a melting point of a solvent −16° C. The solvent of a melting point of a solvent is a solvent of a solution of biocompatible macromolecules.

In the step (b), the solution of the biocompatible macromolecules obtained in the step (a) is frozen. The cooling temperature for the freezing in the step (b) is not particularly limited. Depending on cooling equipment, the cooling temperature is preferably a temperature which is 3° C. to 30° C. lower than the temperature of a portion having the lowest liquid temperature within the solution, more preferably a temperature which is 5° C. to 25° C. lower than the temperature of a portion having the lowest liquid temperature within the solution, and still more preferably a temperature which is 10° C. to 20° C. lower than the temperature of a portion having the lowest liquid temperature within the solution.

In the step (c), the frozen biocompatible macromolecules obtained in the step (b) are freeze-dried. The freeze-drying can be performed through a usual method. For example, the freeze-drying can be performed by carrying out vacuum drying at a temperature lower than a melting point of a solvent and further carrying out vacuum drying at room temperature (20° C.).

In the present invention, a biocompatible macromolecular block can be preferably produced by pulverizing the porous body obtained in the above-described step (c).

(3) Cell

Any cells can be used as the cells used in the present invention as long as it is possible to perform cell transplantation which is the object of the sheet-like cell structure of the present invention, and the types thereof are not particularly limited. In addition, one type of cell may be used, or a plurality of types of cells may be used in combination. In addition, cells to be used are preferably animal cells, more preferably vertebrate-derived cells, and particularly preferably human-derived cells. The types of vertebrate-derived cells (particularly, human-derived cells) may be any of universal cells, somatic stem cells, precursor cells, and mature cells. It is possible to use, for example, embryonic stem (ES) cells, germ-stem (GS) cells, or artificial pluripotent stem (iPS) cells as the universal cells. It is possible to use, for example, mesenchymal stem cells (MSC), hematopoietic stem cells, amniotic cells, umbilical cord blood cells, bone marrow-derived cells, myocardial stem cells, adipose-derived stem cells, or neural stem cells can be used as the somatic stem cell, It is possible to use, for example, skin, dermis, epidermis, muscle, cardiac muscles, nerves, bones, cartilage, endothelium, brain, epithelium, heart, kidney, liver, pancreas, spleen, oral cavity, cornea, bone marrow, umbilical cord blood, amnion, or cells derived from hair as the precursor cells and the mature cells. It is possible to use, for example, ES cells, iPS cells, MSCs, chondrocytes, osteoblasts, osteoprecursor cells, mesenchymal cells, myoblasts, cardiac muscle cells, cardiomyoblasts, nerve cells, hepatocytes, beta cells, fibroblasts, corneal endothelial cells, vascular endothelial cells, corneal epithelial cells, amniotic cells, umbilical cord blood cells, bone marrow-derived cells, or hematopoietic stem cells as the human-derived cells. In addition, the cells may be derived from any of autologous cells and heterologous cells.

For example, it is possible to suitably use, for example, cardiac muscle cells, smooth muscle cells, fibroblasts, skeletal muscle-derived cells (particularly satellite cells), and bone marrow cells (particularly, bone marrow cells differentiated into myocardial-like cells) which are autologous and have been extracted from heterologous cells, in heart diseases such as severe heart failure and severe myocardial infarction. Furthermore, cells for transplantation can be appropriately selected in other organs. Examples of the transplantation include transplantation of neural precursor cells or cells capable of being differentiated into nerve cells into cerebral ischemia or cerebral infarction sites, and transplantation of vascular endothelial cells or cells capable of being differentiated into vascular endothelial cells into myocardial infarction or skeletal muscle ischemia sites.

In addition, examples of the cells to be used for cell transplantation include cells to be used for cell transplantation for diabetic organ disorders. For example, there are cells for cell transplantation therapy in which diseases such as blood circulation disorders in the kidney, the pancreas, peripheral nerves, the eyes, and the limbs are intensively studied. That is, attempts to transplant insulin-secreting cells into the pancreas with a decreased insulin secretion ability, transplantation of bone marrow-derived cells into limbs with circulatory disorders, and the like are have been studied, and such cells can be used.

In the present invention, vascular cells can also be used. In the present specification, the vascular cells mean cells associated with angiogenesis, and are cells forming blood vessels and blood or precursor cells capable of being differentiated into the cells, or somatic stem cells. Here, cells, such as mesenchymal stem cells (MSC) or universal cells such as ES cells, GS cells, or iPS cells, which are not naturally differentiated into and cells forming blood vessels and blood are not included in the vascular cells. The vascular cells are preferably cells forming a blood vessel. In vertebrate-derived cells (particularly, human-derived cells), specific examples of the cells forming blood vessels include vascular endothelial cells and vascular smooth muscle cells. The vascular endothelial cells may be either venous endothelial cells or arterial endothelial cells. Vascular endothelial precursor cells can be used as precursor cells of the vascular endothelial cells. Vascular endothelial cells and vascular endothelial precursor cells are preferably used. Blood cells can be used as the cells forming blood. It is possible to use white blood cells such as lymphocytes or neutrophils, monocyte cells, and hematopoietic stem cells which are stem cells thereof.

In the present specification, non-vascular cells mean cells other than the above-described vascular cells. For example, ES cells, iPS cells, mesenchymal stem cells (MSC), myocardial stem cells, cardiac muscle cells, fibroblasts, myoblasts, chondrocytes, myoblasts, hepatocytes or nerve cells can be used. MSC, chondrocytes, myoblasts, myocardial stem cells, cardiac muscle cells, hepatocytes, or iPS cells can be preferably used. MSC, myocardial stem cells, cardiac muscle cells, or myoblasts can be more preferably used.

(4) Method for Producing Sheet-Like Cell Structure

In the present invention, a sheet-like cell structure is produced through a step of adding biocompatible macromolecular blocks, cells, and a liquid medium onto a culture support body having a plurality of recessed portions on a culture surface, and immersing the biocompatible macromolecular blocks and the cells in uppermost portions of the recessed portions, and a step of culturing the cells to obtain a sheet-like cell structure. A step of peeling the sheet-like cell structure from the culture support body may be optionally included after culturing the cells and obtaining the sheet-like cell structure.

Specifically, a suspension which has been prepared and contain biocompatible macromolecular blocks and cells in a liquid medium may be added onto a culture support body having a plurality of recessed portions to immerse the biocompatible macromolecular blocks and the cells in uppermost portions of the recessed portions.

For example, a proliferation medium or a differentiation medium may be used as the liquid medium.

Examples of the proliferation medium include MSCGM BulletKit (trademark) of Takara Bio Inc. and an EGM-2+ ECFC serum supplement of Lonza, but is not particularly limited.

Examples of the differentiation medium include a mesenchymal stem cell chondrocyte differentiation medium (Mesenchymal Stem Cell Chondrogenic Differentiation Medium) of Takara Bio Inc., a mesenchymal stem cell osteoblast differentiation medium (Mesenchymal Stem Cell Osteogenic Differentiation Medium) of Takara Bio Inc., but is not particularly limited.

Culturing of cells can be carried out optionally in a $CO_2$ incubator. The culture can be carried out generally at 30° C. to 45° C., preferably at 35° C. to 40° C. (for example, 37° C.) for 1 hour to 72 hours, preferably for 1 hour to 24 hours, more preferably for 1 hour to 12 hours, and still more preferably for 2 hours to 8 hours. The culture may be stationary culture or shake culture.

Cells are directly fused with each other and/or cells are fused with each other via biocompatible macromolecular blocks through the above-described culture to produce a sheet-like cell structure.

The size of a sheet-like cell structure to be produced is not particularly limited, but the thickness of the thinnest portion is preferably 50 μm to 5 mm, more preferably 100 μm to 3 mm, and still more preferably 200 μm to 2 mm.

Figure 7:
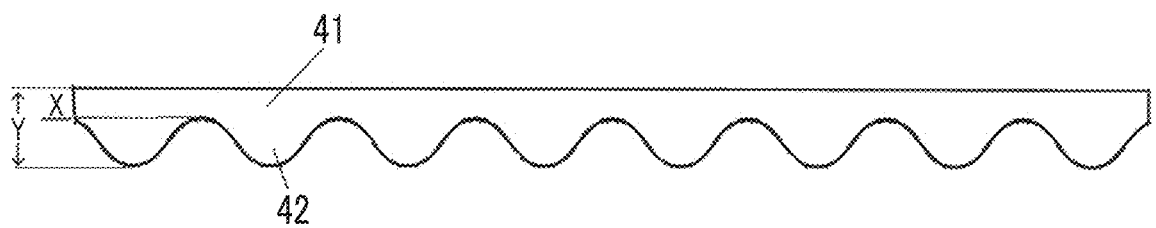
FIG. 7 shows a schematic view of a sheet-like cell structure of the present invention.

A schematic view of a sheet-like cell structure of the present invention is shown in FIG. 7. The sheet-like cell structure is formed of a sheet portion 41 and a plurality of protruding portions 42. The thickness X of the thinnest portion of the sheet-like cell structure indicates the thickness of the sheet portion excluding the protruding portions. The thickness Y of the thickest portion of the sheet-like cell structure indicates the thickness of the thickest portion including the protruding portions of the sheet-like cell structure.

(5) Sheet-Like Cell Structure

The sheet-like cell structure of the present invention is a sheet-like cell structure including: biocompatible macromolecular blocks; and cells, in which the sheet-like cell structure has a plurality of protruding portions on at least a single surface thereof, and a plurality of the above-described biocompatible macromolecular blocks are arranged in gaps between a plurality of the cells in the protruding portions. In a case where the sheet-like cell structure of the present invention has a plurality of protruding portions, the sheet-like cell structure of the present invention exhibits an effect of excellent strength and shape-maintaining performance.

In at least a part of the sheet-like cell structure of the present invention, a plurality of biocompatible macromolecular blocks are arranged in gaps between a plurality of cells. That is, a plurality of biocompatible macromolecular blocks may be arranged in gaps between a plurality of cells in all the sites of the sheet-like cell structure. Alternately, a plurality of biocompatible macromolecular blocks may be arranged in gaps between a plurality of cells in some sites of the sheet-like cell structure, and there may be only cells in other sites of the sheet-like cell structure. In addition, a site where there are only biocompatible macromolecular blocks may be present.

An example of the sheet-like cell structure of the present invention includes a sheet-like cell structure in which a plurality of biocompatible macromolecular blocks are arranged in gaps between a plurality of cells in a lower portion (for example, the protruding portions) of the sheet-like cell structure and there are only cells in an upper portion (for example, the sheet portion) of the sheet-like cell structure.

Another example of the sheet-like cell structure of the present invention includes a sheet-like cell structure in which a plurality of biocompatible macromolecular blocks are arranged in gaps between a plurality of cells in lower portions (for example, the protruding portions) of the sheet-like cell structure and in an upper portion (for example, the sheet portion) of the sheet-like cell structure.

In the present invention, it is preferable that a plurality of biocompatible macromolecular blocks are arranged in gaps between a plurality of cells in at least the protruding portions from the viewpoint of the strength and shape maintenance performance of the sheet-like cell structure.

Since the protruding portions of the sheet-like cell structure are portions formed by the recessed portions of the culture support body, the heights and the diameters of the protruding portions correspond to the depths and the diameters of the recessed portions. However, in some cases, protruding portions of the sheet-like cell structure may shrink during the time between culturing and peeling of cells. Therefore, in some cases, the heights and the diameters of the protruding portions may be smaller than the depths and the diameters of the recessed portions.

The depths of the protruding portions are not particularly limited, but are preferably 10 to 2,000 μm, more preferably 20 to 1,000 μm, still more preferably 30 to 700 μm, still more preferably 50 to 500 μm, and most preferably 100 to 400 μm.

The diameters of the protruding portions are not particularly limited, but are preferably 10 to 2,000 μm, more preferably 50 to 1,500 μm, still more preferably 100 to 1,500 μm, still more preferably 200 to 1,000 μm, and most preferably 400 to 800 μm.

In a case where the protruding portions have the above-described depths and diameters, it is not necessary for all the protruding portions of the sheet-like cell structure to have the above-described depths and diameters, and at least some protruding portions may have the above-described depths and diameters.

The shapes (including the depths and the diameters) of the protruding portions may be uniform or nonuniform, but are preferably uniform. It is preferable that the depths and diameters of the protruding portions are uniform, and it is preferable that the depths and diameters of all the protruding portions are substantially the same.

The thickness of the thinnest portion of the sheet-like cell structure is as described above in the present specification.

In the present invention, a plurality of biocompatible macromolecular blocks are three-dimensionally arranged in gaps between a plurality of cells in a mosaic shape using the biocompatible macromolecular blocks and the cells. Accordingly, it is possible to deliver nutrients to the inside of the cell structure from the outside.

In at least a part of the cell structure of the present invention, the plurality of biocompatible macromolecular blocks are arranged in gaps between the plurality of cells. Here, the "gaps between cells" is not necessarily a space closed by the constituent cells, and may be interposed by the cells. Gaps are not necessarily present between all of the cells, and there may be a place where cells are brought into contact with each other. The distance of gaps between cells through biocompatible macromolecular blocks, that is, the gap distance in a case of selecting a certain cell, and a cell existing in a shortest distance from the certain cell is not particularly limited. However, the distance is preferably the size of a biocompatible macromolecular block, and a favorable distance is also within the range of the favorable size of a biocompatible macromolecular block.

In addition, the biocompatible macromolecular blocks have a configuration of being interposed by the cells. However, there are not necessarily cells between all of the biocompatible macromolecular blocks, and there may be a place where biocompatible macromolecular blocks are brought into contact with each other. The distance between biocompatible macromolecular blocks through cells, that is, the distance in a case of selecting a biocompatible macromolecular block, and a biocompatible macromolecular block existing in a shortest distance from the biocompatible macromolecular block is not particularly limited. However, the distance is preferably the size of an aggregation of cells in a case where one or several cells to be used are gathered. For example, the size thereof is 10 μm to 1,000 μm, preferably 10 μm to 500 μm, and more preferably 10 μm to 200 μm.

In the sheet-like cell structure in the present invention, the ratio of a biocompatible macromolecular block to a cell is not particularly limited. However, the ratio of a biocompatible macromolecular block per cell is preferably 0.0000001 μg to 1 μg, more preferably 0.000001 μg to 0.1 μg, still more preferably 0.00001 μg to 0.01 μg, and most preferably 0.00002 μg to 0.006 μg. By setting the ratio of the biocompatible macromolecular blocks to the cells to be within the above-described range, it is possible to make the cells more evenly exist. By setting the lower limit to be within the above-described range, it is possible to exhibit an effect of the cells in a case of using the cells for a desired purpose. Moreover, by setting the upper limit to be within the above-described range, it is possible to supply components in arbitrarily existing biocompatible macromolecular blocks to cells. Here, the components in biocompatible macromolecular blocks are not particularly limited, but examples thereof include components contained in a liquid medium.

(6) Use of Sheet-Like Cell Structure

The sheet-like cell structure of the present invention can be used for cell transplantation. Specifically, the sheet-like cell structure of the present invention can be used for the purpose of transplanting cells into sites with heart diseases such as severe heart failure and severe myocardial infarction and diseases such as cerebral ischemia and cerebral infarction. In addition, the cell structure of the present invention can also be used for diabetic diseases such as blood circulation disorders in the kidney, the pancreas, the liver, peripheral nerves, the eyes, and the limbs.

As the transplantation method, it is possible to use incision and a method using an endoscope.

In addition, according to the present invention, there is provided a cell transplantation method including a step of transplanting the sheet-like cell structure of the present invention into a patient who requires cell transplantation. In the cell transplantation method, the sheet-like cell structure of the present invention described above is used. The suitable range of the sheet-like cell structure is the same as described above.

According to the present invention, use of the sheet-like cell structure of the present invention for producing a cell transplantation treatment agent is further provided. According to the present invention, the suitable range of the sheet-like cell structure is preferably the same as described above.

According to the present invention, a cell transplantation treatment agent containing the sheet-like cell structure of the present invention is further provided. According to the present invention, the suitable range of the sheet-like cell structure is the same as described above.

The present invention will be more specifically described using the following examples, but is not limited by the examples.

EXAMPLES

Example 1

Recombinant Peptide (Recombinant Gelatin)

The following CBE3 (which is disclosed in WO2008/103041A) was prepared as recombinant peptides (recombinant gelatin).
CBE3:
Molecular weight: 51.6 kD
Structure:

GAP[(GXY)$_{63}$]$_3$G  (SEQ ID NO: 11)

Number of amino acids: 571
RGD sequence: 12
Imino acid content: 33%

Almost 100% of amino acids have a repeating structure of GXY. In the amino acid sequence of CBE3, serine, threonine, asparagine, tyrosine, and cysteine are not included. CBE3 has an ERGD sequence.
Isoelectric point: 9.34
GRAVY value: −0.682
1/IOB value: 0.323

Amino acid sequence (SEQ ID No: 1 in a sequence table) (which is the same as that of SEQ ID No: 3 in WO2008/103041A. However, X in the end is corrected to "P").

(SEQ ID NO: 1)
GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)$_3$G

Example 2

Production of Porous Body of Recombinant Peptide

[PTFE Thickness•Cylindrical Container]
A cylindrical cup-shaped polytetrafluoroethylene (PTFE) container with a bottom surface thickness of 3 mm, a diameter of 51 mm, a side surface thickness of 8 mm, and a height of 25 mm was prepared. In a case where the curved surface of the cylindrical cup is set as a side surface, the side surface is closed by PTFE with 8 mm and the bottom surface (circular shape of a flat plate) is also closed by PTFE with 3 mm. In contrast, the upper surface is in an open shape. Accordingly, the inner diameter of the cylindrical cup is set to 43 mm. Hereinafter, this container is referred to as a PTFE thickness•cylindrical container.

[Aluminum Glass Plate•Cylindrical Container]
A cylindrical cup-shaped aluminum container with a thickness of 1 mm and a diameter of 47 mm was prepared. In a case where the curved surface of the cylindrical cup is set as a side surface, the side surface is closed by aluminum with 1 mm and the bottom surface (circular shape of a flat plate) is also closed by aluminum with 1 mm. In contrast, the upper surface is in an open shape. In addition, TEFLON (registered trademark) with a thickness of 1 mm is evenly spread only in the inside of the side surface, and as a result, the inner diameter of the cylindrical cup becomes 45 mm. In addition, the bottom surface of this container enters a state where a 2.2 mm glass plate is joined to the bottom surface thereof on the outside of aluminum. Hereinafter, this container is referred to as an aluminum glass•cylindrical container.

[Freezing Step in which Difference in Temperature is Small, and Drying Step]
An aqueous CBE3 solution was made to flow into the PTFE thickness•cylindrical container and the aluminum glass plate•cylindrical container, and was cooled down from the bottom surface within a vacuum freeze dryer (TF5-85ATNNN: Takara Co., Ltd.) using a cooling shelf. A combination of the setting of the final concentration of the aqueous CBE3 solutions in the containers at this time, the amount of solution, and the temperature of the shelf was prepared as described below.

Condition A:
PTFE thickness•cylindrical container, final concentration of aqueous CBE3 solution of 4 mass %, amount of aqueous solution of 4 mL. As the setting for the temperature of the shelf, the temperature was cooled down until the temperature reaches −10° C., and then, freezing was performed for 1 hour at −10° C., for 2 hours at −20° C., for 3 hours at −40° C., and finally for 1 hour at −50° C. Thereafter, the frozen product was subjected to vacuum drying for 24 hours at −20° C. after the setting of the temperature of the shelf was returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased (1.9×10$^5$ Pa). Then, the product was taken out of the vacuum freeze dryer. Accordingly, a porous body was obtained.

Condition B:
Aluminum•glass plate•cylindrical container, final concentration of aqueous CBE3 solution of 4 mass %, amount of aqueous solution of 4 mL. As the setting for the temperature of the shelf, the temperature was cooled down until the temperature reaches −10° C., and then, freezing was performed for 1 hour at −10° C., for 2 hours at −20° C., for 3 hours at −40° C., and finally for 1 hour at −50° C. Thereafter, the frozen product was subjected to vacuum drying for 24 hours at −20° C. after the setting of the temperature of the shelf was returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased (1.9×10$^5$ Pa). Then, the product was taken out of the vacuum freeze dryer. Accordingly, a porous body was obtained.

Condition C:
PTFE thickness•cylindrical container, final concentration of aqueous CBE3 solution of 4 mass %, amount of aqueous solution of 10 mL. As the setting for the temperature of the shelf, the temperature was cooled down until the temperature reaches −10° C., and then, freezing was performed for 1 hour at −10° C., for 2 hours at −20° C., for 3 hours at −40° C., and finally for 1 hour at −50° C. Thereafter, the frozen product was subjected to vacuum drying for 24 hours at −20°

C. after the setting of the temperature of the shelf was returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased (1.9×10$^5$ Pa). Then, the product was taken out of the vacuum freeze dryer. Accordingly, a porous body was obtained.

[Measurement of Temperature in Each Freezing Step]

Regarding the conditions A to C, the liquid temperature of the surface of water in a center portion of a circle within a container was measured as the liquid temperature (non-cooled surface liquid temperature) of the farthest portion from a cooling side in a solution, and the liquid temperature of a bottom portion within the container was measured as the liquid temperature (cooled surface liquid temperature) of the closest portion to the cooling side in the solution.

Figure 8:
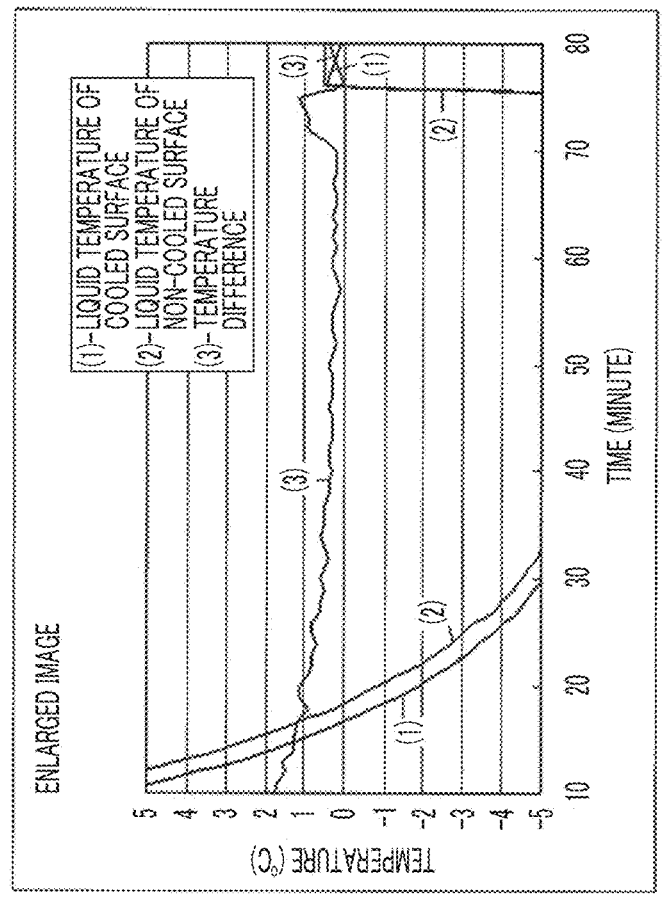
FIG. 8 shows a liquid temperature profile of a condition A of examples.
Figure 8:
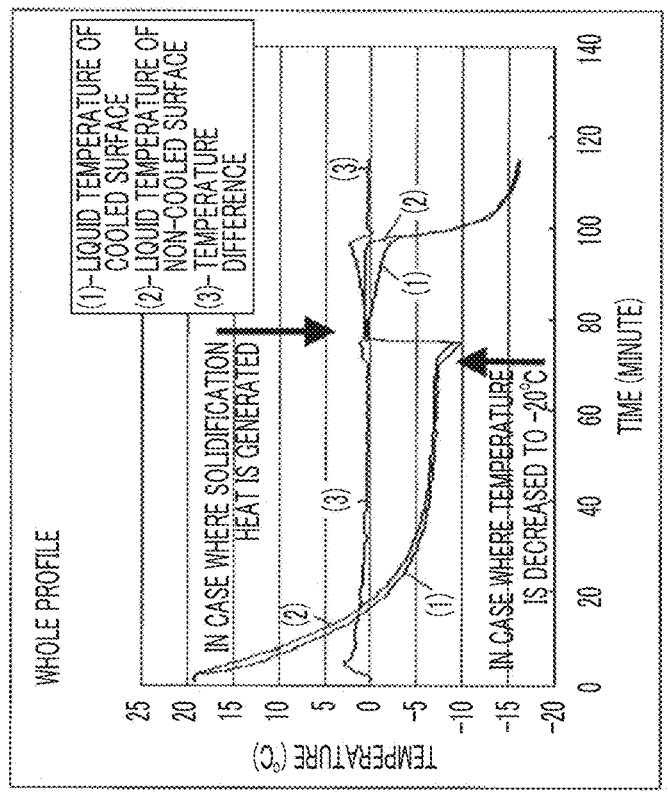
Figure 9:
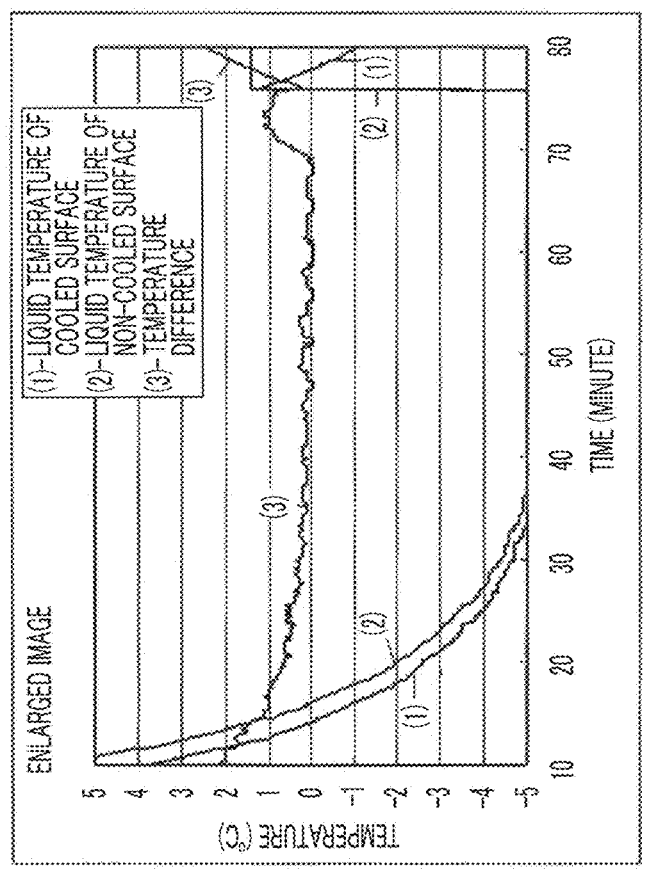
FIG. 9 shows a liquid temperature profile of a condition B of examples.
Figure 9:
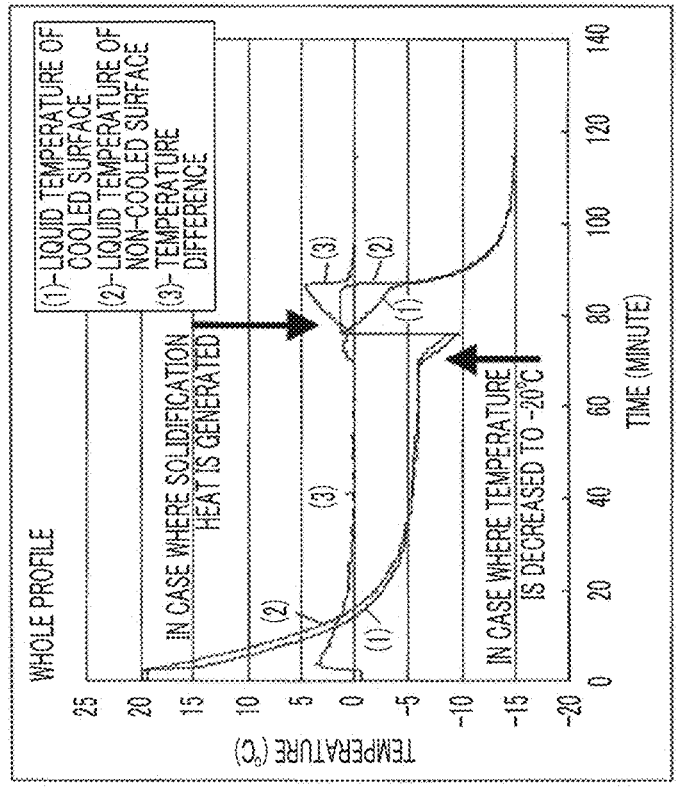
Figure 10:
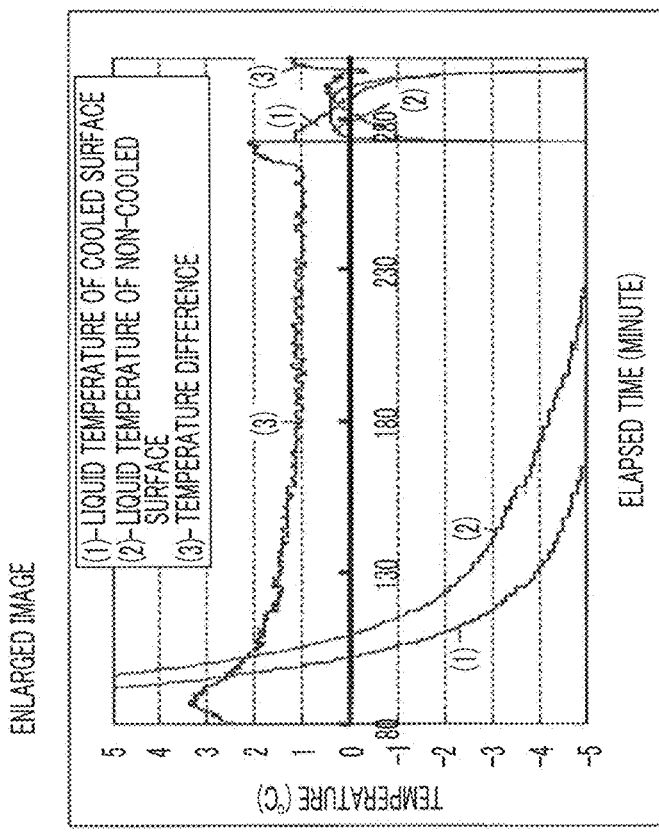
FIG. 10 shows a liquid temperature profile of a condition C of examples.
Figure 10:
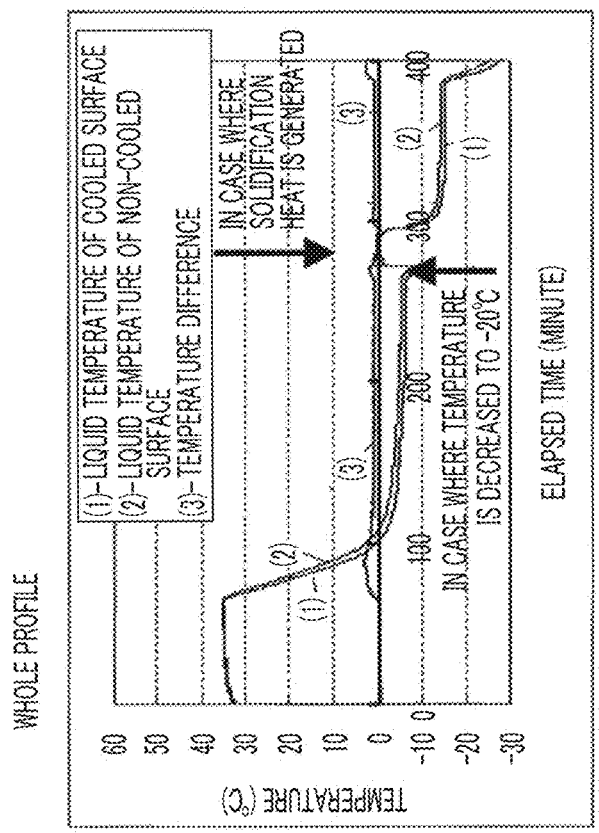

As a result, each temperature and a profile of the difference in temperature are as shown in FIGS. 8 to 10.

It can be seen from FIGS. 8 to 10 that the liquid temperature falls below 0° C., which is a melting point, in a setting section of the temperature of a shelf of −10° C. (before the temperature decreases to −20° C.) in the conditions A to C, and the solution enters a (unfrozen and overcooled) state where freezing does not occur in that state. In addition, in this state, the difference in temperature between the cooled surface liquid temperature and the non-cooled surface liquid temperature is less than or equal to 2.5° C. In the present specification, the "difference in temperature" means "non-cooled surface liquid temperature"–"cooled surface liquid temperature". Thereafter, the timing at which the liquid temperature rapidly rises to around 0° C. by further lowering the temperature of the shelf to −20° C. is confirmed. Here, it can be seen that freezing starts due to generation of solidification heat. In addition, it was also possible to confirm that ice formation actually started at the timing. Thereafter, the temperature was around 0° C. while the certain time passes. Here, the product entered a state where there was a mixture of water and ice. The temperature finally started to decrease again from 0° C. Accordingly, the temperature being measured became a solid temperature within the ice, that is, was not the liquid temperature.

Hereinafter, regarding the conditions A to C, the difference in temperature at this time when the non-cooled surface liquid temperature became a melting point (0° C.), the difference in temperature immediately before the temperature of the shelf is decreased from −10° C. to −20° C., and the difference in temperature immediately before the generation of solidification heat will be described. The "difference in temperature immediately before" referred in the present invention indicates the highest temperature in the difference in temperature which can be detected between 1 second to 20 seconds before an event (such as the generation of solidification heat).

Condition A:

Difference in temperature at this time when non-cooled surface liquid temperature became melting point (0° C.): 1.1° C.

Difference in temperature immediately before temperature is decreased from −10° C. to −20° C.:0.2° C.

Difference in temperature immediately before generation of solidification heat: 1.1° C.

Condition B:

Difference in temperature at this time when non-cooled surface liquid temperature became melting point (0° C.):1.0° C.

Difference in temperature immediately before temperature is decreased from −10° C. to −20° C.:0.1° C.

Difference in temperature immediately before generation of solidification heat: 0.9° C.

Condition C:

Difference in temperature at this time when non-cooled surface liquid temperature became melting point (0° C.):1.8° C.

Difference in temperature immediately before temperature is decreased from −10° C. to −20° C.:1.1° C.

Difference in temperature immediately before generation of solidification heat: 2.1° C.

Example 3

Production of Biocompatible Macromolecular Block (Pulverizing and Cross-Linking of Porous Body)

The CBE3 porous bodies which had been obtained in Example 2 were pulverized using NEW POWERMILL (Osaka Chemical Co., Ltd., NEW POWERMILL PM-2005). The pulverizing was performed for one minute×5 times, that is, for 5 minutes in total at the maximum rotation speed. The sizes of the obtained pulverized substances were divided using a stainless steel sieve to obtain uncross-linked blocks with 25 to 53 μm, 53 to 106 μm, and 106 to 180 μm. Thereafter, biocompatible macromolecular blocks (CBE3 blocks) were obtained by performing thermal cross-linking (six kinds of cross-linking times of 8 hours, 16 hours, 24 hours, 48 hours, 72 hours, and 96 hours) at 160° C. under reduced pressure.

Hereinafter, a porous body-derived block under the condition A which has been cross-linked for 48 hours is called E, and a porous body-derived block under the condition B which has been cross-linked for 48 hours is called F, E and F are blocks with a small difference in temperature which have been produced from porous bodies produced through a freezing step in which the difference in temperature is small. There was no influence of the difference in cross-linking time on the performance in the evaluation of the present specification. Therefore, the blocks cross-linked for 48 hours were representatively used. In addition, there was no difference in performance between E and F. Hereinafter, the biocompatible macromolecular blocks obtained in Example 3 are also referred to as "petal blocks". In examples and comparative examples, biocompatible macromolecular blocks which have sizes of 53 to 106 μm, are produced under the condition A, and of which the cross-linking time is 48 hours were used.

Example 4

Measurement of Tap Density of Biocompatible Macromolecular Block

The tap density is a value indicating how much volume of block can be densely filled. It can be said that, as the value becomes smaller, the block cannot be densely filled, that is, the structure of the block is complicated. The tap density was measured as follows. First, a funnel with an attached cap (having a cylindrical shape with a diameter of 6 mm and a length of 21.8 mm: capacity of 0.616 cm$^3$) at the tip thereof was prepared, and the mass of only the cap was measured. Thereafter, the cap was attached to the funnel, and blocks were poured from the funnel so as to be collected in the cap. After placing a sufficient amount of block, the cap portion was hit 200 times on a hard object such as a desk, the funnel was removed, and the blocks were leveled with a spatula. The mass was measured in a state where the cap was filled up with the blocks. The tap density was obtained by calculating the mass of only the blocks from the difference between the mass of the cap filled up with the blocks and the mass of only the cap, and dividing the mass of only the blocks by the volume of the cap.

As a result, the tap density of the biocompatible macromolecular blocks of Example 3 is 98 mg/cm$^3$.

Example 5

Measurement of Cross-Linking Degree of Biocompatible Macromolecular Block

The cross-linking degree (the number of cross-linking times per molecule) of the blocks cross-linked in Example 3 was calculated. The measurement was performed through a TNBS (2,4,6-trinitrobenzene sulfonic acid) method.
<Preparation of Sample>
A sample (about 10 mg), 4% NaHCO$_3$ aqueous solution (1 mL), and 1 mass % TNBS aqueous solution (2 mL) were added to a glass vial, and the mixture was shaken for 3 hours at 37° C. Thereafter, 37 mass % hydrochloric acid (10 mL) and pure water (5 mL) were added thereto, and then, the mixture was allowed to stand for 16 hours or longer at 37° C. to prepare a sample.
<Preparation of Blank>
A blank (about 10 mg), 4 mass % NaHCO$_3$ aqueous solution (1 mL), and 1 mass % TNBS aqueous solution (2 mL) were added to a glass vial, 37 mass % hydrochloric acid (3 mL) was immediately added thereto, and the mixture was shaken for 3 hours at 37° C. Thereafter, 37 mass % hydrochloric acid (7 mL) and pure water (5 mL) were added thereto, and then, the mixture was allowed to stand for 16 hours or longer at 37° C. to prepare a blank.

The absorbance (345 nm) of the sample and the blank which had been diluted 10 times with pure water was measured, and the cross-linking degree (the number of cross-linking times per molecule) was calculated from (Formula 2) and (Formula 3).

$(As-Ab)/14,600 \times V/w$ (Formula 2)

(Formula 2) represents the amount (molar equivalent) of lysine per 1 g of recombinant peptide.
(in the formula, As represents the sample absorbance, Ab represents the blank absorbance, V represents the amount (g) reaction liquid, and w represents the mass (mg) of recombinant peptide.)

1−(sample(Formula 2)/uncross-linked recombinant peptide(Formula 2))×34 (Formula 3)

(Formula 3) represents the number of cross-linking times per molecule.

As a result, the cross-linking degree of the biocompatible macromolecular blocks of Example 3 is 4.2.

Example 6

Measurement of Water Absorption Rate of Biocompatible Macromolecular Block

The water absorption rate of biocompatible macromolecular blocks produced in Example 3 was calculated.
A 3 cm×3 cm nylon mesh bag was filled with about 15 mg of the biocompatible macromolecular blocks at 25° C. and was swollen in ion exchange water for 2 hours. Then, the biocompatible macromolecular blocks were dried with air for 10 minutes, and the mass was measured at each stage to obtain the water absorption rate according to (Formula 4).

Water absorption rate=(w2−w1−w0)/w0 (Formula 4)

(in the formula, w0 represents the mass of a material before water absorption, w1 represents the mass of an empty bag after water absorption, and w2 represents the mass of the entirety of the bag containing the material after water absorption.)

As a result, the water absorption rate of the blocks of Example 3 is 786%.

Example 7

Production of Sheet-Like Cell Structure Having Protruding Portion (Sheet-Like Mosaic Cell Aggregation Having Protruding Portion)

Human bone marrow-derived mesenchymal stem cells (hMSCs) were suspended in a proliferation medium (Takara Bio Inc.: MSCGM Bullet Kit (trademark)), and biocompatible macromolecular blocks (53 to 106 μm) prepared in Example 3 were added thereto. The mixture was sown in EZSPHERE (registered trademark) DISH 35 mm Type 903 (which had a spheroid well diameter of 800 μm, a spheroid well depth of 300 μm, and about 1,000 spheroid wells, and was manufactured by AGC TECHNO GLASS CO., Ltd.) which was a cell non-adhesive 35 mm dish having recessed portions on its bottom surface, in a state in which hMSCs (2×10$^7$ cells) and biocompatible macromolecular blocks (20 mg) were finally suspended in 4 mL of a medium. In the EZSPHERE (registered trademark) DISH 35 mm Type 903, the area of the recessed portions on the culture surface is 100% with respect to the whole area of the culture surface, and the surface of the culture support body between mutually adjacent recessed portions is non-flat.

Figure 11:
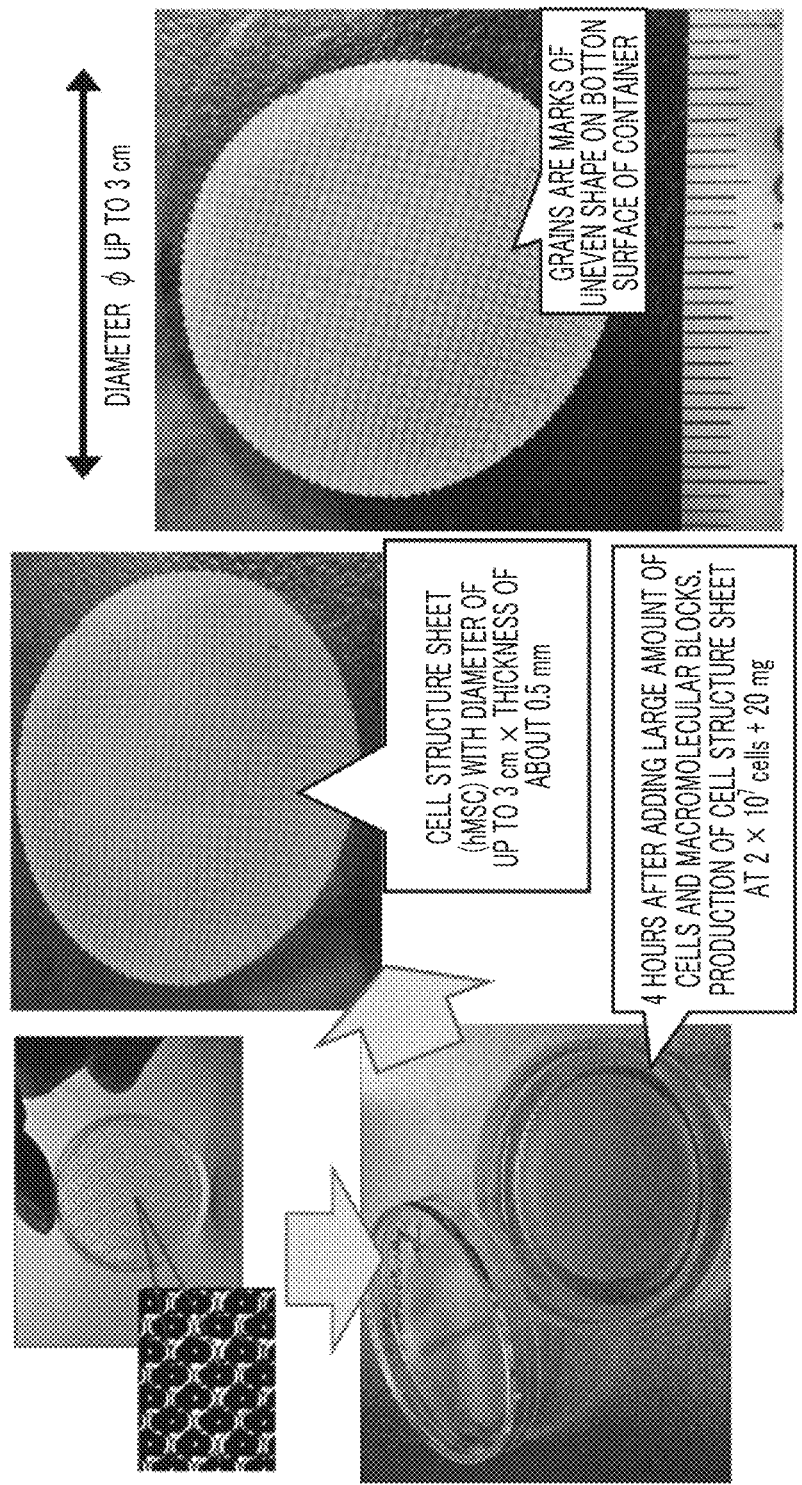
FIG. 11 shows a result of producing a sheet-like cell structure having protruding portions.

The dish was allowed to stand in a CO$_2$ incubator at 37° C. for 4 hours, and as a result, it was possible to produce and collect a sheet-like cell structure which has protruding portions was produced in a disk sheet shape having a diameter of about 30 mm and a thickness of about 500 μm and is formed of hMSCs and biocompatible macromolecular blocks (FIG. 11). It was found that the sheet-like cell structure having these protruding portions has sufficient strength and can maintain its shape without rolling. In the thus obtained sheet-like cell structure having the protruding portions, the thickest portion was about 500 μm and the thinnest portion was about 150 μm. The sheet-like cell structure having protruding portions which was obtained through this method is a sheet-like cell structure in which cells and blocks coexist in the protruding portions obtained due to the shape of the cell support body having recessed portions, and there are only cells in a flat portion on a reverse surface side.

In addition, 5×10$^7$ cells of hMSCs and 50 mg of biocompatible macromolecular blocks were suspended in 4 mL of a medium and sown in the same EZSPHERE (registered trademark) DISH 35 mm Type 903, and was allowed to stand in an incubator for 4 hours in the same manner. As a result, it was possible to obtain and collect a sheet-like cell structure having protruding portions in a disk sheet shape having a diameter of about 30 mm and a thickness of about 1.4 mm. In the thus obtained sheet-like cell structure having the protruding portions, the thickest portion was about 1.4 mm and the thinnest portion was about 500 μm. The sheet-like cell structure having protruding portions which was obtained through this method is a sheet-like cell structure in which cells and blocks coexist in the protruding portions obtained due to the shape of the cell structure having recessed portions, and coexist also in a flat portion on a reverse surface side.

It was confirmed that it was possible to produce a sheet-like cell structure (a sheet-like mosaic cell aggregation having protruding portions) having protruding portions in the same manner using any one of Type 900 (with a well diameter of 400 to 500 µm and a well depth of 100 to 200 µm), Type 902 (with a well diameter of 500 µm and a well depth of 200 µm), and Type 904 (with a well diameter of 800 µm and a well depth of 400 µm) as a dish to be used. It was found that the sheet-like cell structure having protruding portions has sufficient strength and can maintain its shape without rolling under any conditions. In the Type 900, Type 902, and Type 904 dishes, the area of the recessed portions on the culture surface is 100% with respect to the whole area of the culture surface, and the surface of the culture support body between mutually adjacent recessed portions is non-flat.

Regarding the evaluation of the strength, it was possible to confirm that transplantation could be performed without any breakage in a case where the sheet-like cell structure having protruding portions which was produced using hMSCs ($2 \times 10^7$ cells) and biocompatible macromolecular blocks (20 mg) in an EZSPHERE (registered trademark) DISH 35 mm Type 903 container was lifted in order to be attached to the surface of an organ using forceps. Therefore, it was found that the sheet-like cell structure had sufficient strength.

As described above, it was found that it was possible to simply produce a thick sheet-like cell structure by placing cells and biocompatible macromolecular blocks in a cell support body having recessed portions on its bottom surface.

Comparative Example 1

Production of Flat Sheet-Like Cell Structure (Flat Sheet-Like Mosaic Cell Aggregation)

Human bone marrow-derived mesenchymal stem cells (hMSCs) were suspended in a proliferation medium (Takara Bio Inc.: MSCGM Bullet Kit (trademark)), and biocompatible macromolecular blocks (53 to 106 µm) prepared in Example 3 were added thereto. The mixture was sown in PrimeSurface Dish (manufactured by Sumitomo Bakelite Co., Ltd.) with a diameter of 35 mm which was a cell non-adhesive 35 mm dish having a flat bottom surface, in a state in which hMSCs ($2 \times 10^7$ cells) and biocompatible macromolecular blocks (20 mg) were finally suspended in 4 mL of a medium.

The dish was allowed to stand in a $CO_2$ incubator at 37° C. for 4 hours, and as a result, it was possible to produce and collect a flat sheet-like cell structure in a disk sheet shape having a diameter of about 30 mm and a thickness of about 500 µm and is formed of hMSCs and biocompatible macromolecular blocks. However, it was found that there are defects in that the flat sheet-like cell structure has weak strength, tears easily, and is easily rolled compared to the sheet-like cell structure with protruding portions in Example 7 which has sufficient strength and maintains its shape.

Sheet-like cell structures at cell concentrations $2 \times 10^7$ cells to $8 \times 10^7$ cells were produced through by shaking a mixture. It was confirmed that it was possible to produce flat sheet-like cell structures (flat sheet-like mosaic cell aggregations) in the same manner using any one of the concentrations. However, regarding the properties, it was confirmed, as a coincident result, that the flat sheet-like cell structures had weak strength, tore easily, and were easily rolled compared to the sheet-like cell structure with protruding portions in Example 7.

Regarding the evaluation of the strength, in a case where the flat sheet-like cell structure produced using hMSCs ($2 \times 10^7$ cells) and biocompatible macromolecular blocks (20 mg) in a PrimeSurface Dish container with a diameter of 35 mm was lifted in order to be attached to the surface of an organ using forceps, the flat sheet-like cell structure easily broke and it was difficult to perform transplantation as it is compared to the sheet-like cell structure having protruding portions in Example 7. Therefore, it was found that the flat sheet-like cell structure did not have sufficient strength.

Comparative Example 2

Production of Cell Sheet (Only with Cell) Having Protruding Portion

Human bone marrow-derived mesenchymal stem cells (hMSCs) were suspended in a proliferation medium (Takara Bio Inc.: MSCGM Bullet Kit (trademark)). The mixture was sown in EZSPHERE (registered trademark) DISH 35 mm Type 903 (which had a spheroid well diameter of 800 µm, a spheroid well depth of 300 µm, and about 1,000 spheroid wells, and was manufactured by AGC TECHNO GLASS CO., Ltd.) which was a cell non-adhesive 35 mm dish having recessed portions on its bottom surface, in a state in which hMSCs ($8 \times 10^7$ cells) were finally suspended in 4 mL of a medium.

The dish was allowed to stand in a $CO_2$ incubator at 37° C. for 4 hours, and as a result, it was found that the hMSCs remained in a suspension state, and could not be collected as a form of a sheet-like cell structure.

In addition, the dish to be used was changed to Type 900 (with a well diameter of 400 to 500 µm and a well depth of 100 to 200 µm), Type 902 (with a well diameter of 500 µm and a well depth of 200 µm), and Type 904 (with a well diameter of 800 µm and a well depth of 400 µm) to attempt the production of cell sheets at cell concentrations $2 \times 10^7$ cells to $8 \times 10^7$ cells by shaking a mixture. However, it was impossible to produce cell sheets having protruding portions in any cases. Accordingly, it was found that it was impossible to produce cell sheets having protruding portions using a cell support body having recessed portions on its bottom surface.

Comparative Example 3

Production of Flat Cell Sheet (Only with Cell)

Human bone marrow-derived mesenchymal stem cells (hMSCs) were suspended in a proliferation medium (Takara Bio Inc.: MSCGM Bullet Kit (trademark)). The mixture was sown in PrimeSurface Dish (manufactured by Sumitomo Bakelite Co., Ltd.) with a diameter of 35 mm which was a cell non-adhesive 35 mm dish having a flat bottom surface, in a state in which hMSCs ($2 \times 10^7$ cells) and were finally suspended in 4 mL of a medium.

The dish was allowed to stand in a $CO_2$ incubator at 37° C. for 4 hours, and as a result, it was possible to produce and collect a flat cell sheet in a disk sheet shape having a diameter of about 20 mm and a thickness of about 300 µm and is formed of only hMSCs. However, the flat cell sheet had significantly weak strength and was hardly lifted compared to the sheet-like cell structure with the protruding portions in Example 7 which had sufficient strength and maintained its shape. Since the flat cell sheet shrunk at a significantly high speed, the diameter of the flat cell sheet shrunk to 20 mm during the formation of the flat cell sheet for 4 hours. Therefore, it was found that it was impossible to maintain the initial shape of the flat cell sheet. It can be seen that it is impossible to maintain the size of the flat cell sheet compared to the case where it is possible to maintain the size of the flat sheet-like cell structure of Comparative Example 1.

Cell sheets at cell concentrations $2 \times 10^7$ cells to $8 \times 10^7$ cells were produced through by shaking a mixture. It was confirmed that it was possible to produce flat cell sheets (only with cells) in the same manner using any one of the concentrations. However, regarding the properties, the facts that the strength of the flat cell sheets was significantly weak and was hardly lifted compared to the sheet-like cell structure with the protruding portions in Example 7 which had sufficient strength and maintained its shape were not changed. Similarly, the flat cell sheets shrunk at a significantly high speed, and therefore, the diameters of the flat cell sheets shrunk to 20 mm during the formation of the flat cell sheets for 4 hours. Thus, it was impossible to maintain the initial shapes of the flat cell sheets. It was found that it was impossible to maintain the sizes of any of the flat cell sheets compared to the case where it was possible to maintain the size of the flat sheet-like cell structure of Comparative Example 1.

Summary of Results of Examples and Comparative Examples

The results of the sheet-like cell structure with protruding portions produced in Example 7, the flat sheet-like cell structure produced in Comparative Example 1, the cell sheet with protruding portions that could not be produced in Comparative Example 2, and the flat cell sheets produced in Comparative Example 3 are shown in FIG. 12 and Table 1.

From the obtained results, it can be seen that it is impossible to produce a cell sheet using a cell support body having recessed portions on its bottom surface, whereas it is possible to form a cell sheet using a cell support body with a flat bottom surface in the process of making a cell sheet or cell aggregation only with cells. From the unexpected results, it can be seen that, in the cell structure formed of cells and biocompatible macromolecular blocks, it is possible to form a sheet-like cell structure even with the cell support body having a flat bottom surface or the cell support body having recessed portion on its bottom surface. Furthermore, it can be unexpectedly seen that, in the cell structure formed of cells and biocompatible macromolecular blocks, the sheet-like cell structure with protruding portions which has been produced using a cell support body having recessed portions on its bottom surface becomes a sheet-like cell structure having sufficient strength, easily maintaining its shape, and having favorable handleability, contrary to the results (comparative example) of the case only with cells.

EXPLANATION OF REFERENCES

1: culture support body
10: container main body
12: lid
14: bottom plate portion
16: side wall portion
20: recessed portion
24: well formation region
30: cell adhesion suppressant layer
41: sheet portion
42: protruding portion
X: thickness of thinnest portion
Y: thickness of thickest portion

TABLE 1

|  | Cell structure containing cells and biocompatible macromolecular blocks | Only cells |
|---|---|---|
| Sheet with protruding portions which has been produced using cell support body having recessed portions on its surface | Example 7: Favorable handleability (without breakage) Favorable shape-maintaining performance (without shrinkage) Comprehensive evaluation: A | Comparative Example 2: Cells are not fused, and therefore, sheet cannot be produced. Comprehensive evaluation: D |
| Flat sheet produced using cell support body having flat surface | Comparative Example 1: Handleability is slightly bad (it is easily cracked and rolled compared to sheet-like cell structure having protruding portions of cell structure) Favorable shape-maintaining performance (without shrinkage) Comprehensive evaluation: B | Comparative Example 3: Bad handleability (easily broken) Bad shape-maintaining performance (shrunk) Comprehensive evaluation: C |

[Sequence Table]

International Application 16F00427 Method for Producing Sheet-Like Cell Structure JP16078779 20160929----00130322351602033566 Normal 20160929115114201609091041266760_P1AP101_16_1.app Based on International Patent Cooperation Treaty

What is claimed is:

1. A method for producing a sheet-like cell structure, comprising:
   adding a biocompatible macromolecular block, a cell, and a liquid medium onto a culture support body having a plurality of recessed portions on a culture surface, and immersing the biocompatible macromolecular block and the cell in uppermost portions of the recessed portions; and
   culturing the cell to obtain a sheet-like cell structure which maintains its shape and resists rolling;
   wherein the culture surface of the culture support body is subjected to a treatment for suppressing adhesion of cells,
   the area of the recessed portions on the culture surface is larger than or equal to 70% with respect to the whole area of the culture surface, and
   the recessed portions have a depth of from 10 µm to 2,000 µm.

2. The method for producing a sheet-like cell structure according to claim 1,
   wherein the recessed portions have a diameter of from 10 µm to 2,000 µm, and a circular shape.

3. The method for producing a sheet-like cell structure according to claim 1,
   wherein a thickness of a thinnest portion of the sheet-like cell structure is 50 µm to 5 mm.

4. The method for producing a sheet-like cell structure according to claim 1,
   wherein a size of the biocompatible macromolecular block is 1 µm to 700 nm.

5. The method for producing a sheet-like cell structure according to claim 1,
   wherein biocompatible macromolecules are recombinant gelatin.

6. The method for producing a sheet-like cell structure according to claim 5, wherein the recombinant gelatin is any one of a peptide formed of an amino acid sequence described in SEQ ID NO: 1;

a peptide which is formed of an amino acid sequence in which one or several amino acids are deleted, substituted, or added in the amino acid sequence described in SEQ ID NO: 1, and has biocompatibility; and a peptide which is formed of an amino acid sequence having 90% or more sequence identity to the amino acid sequence described in SEQ ID NO: 1, and has biocompatibility.

7. The method for producing a sheet-like cell structure according to claim 1, wherein the cells are cultured at 35° C. to 40° C.

8. The method for producing a sheet-like cell structure according to claim 1, wherein the recessed portions are circular, and have a depth of 100 μm to 2,000 μm and a diameter of 200 μm to 2,000 μm.

9. A sheet-like cell structure comprising:

a biocompatible macromolecular block; and a cell, wherein the sheet-like cell structure has a plurality of protruding portions on at least a single surface thereof, and a plurality of the biocompatible macromolecular blocks are arranged in gaps between a plurality of the cells in the protruding portions;

the sheet-like cell structure maintains its shape and resists rolling;

the protruding portions have a height of from 10 μm to 2,000 μm; and the protruding portions have an area that is larger than or equal to 70% with respect to the area of said single surface of the sheet-like cell structure.

10. The sheet-like cell structure according to claim 9, further comprising:

protruding portions having a height of 10 μm to 2,000 μm and a diameter of 10 μm to 2,000 μm.

11. The sheet-like cell structure according to claim 9, wherein the protruding portions have a height of 100 μm to 2,000 μm and a diameter of 200 μm to 2,000 μm.

* * * * *